(12) United States Patent
Tao et al.

(10) Patent No.: US 9,993,175 B2
(45) Date of Patent: Jun. 12, 2018

(54) PULSED ULTRA-WIDEBAND SENSOR AND THE METHOD THEREOF

(71) Applicant: INDUSTRIAL TECHNOLOGY RESEARCH INSTITUTE, Hsinchu (TW)

(72) Inventors: Teh Ho Tao, Hsinchu (TW); Igor Yakovlevich Immoreev, Moscow (RU); Maksim Vladimirovich Fesenko, Moscow (RU)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 304 days.

(21) Appl. No.: 14/802,650

(22) Filed: Jul. 17, 2015

(65) Prior Publication Data

US 2015/0320336 A1 Nov. 12, 2015

Related U.S. Application Data

(63) Continuation of application No. 12/388,264, filed on Feb. 18, 2009, now abandoned.

(30) Foreign Application Priority Data

Feb. 20, 2008 (RU) ................................ 2008106039

(51) Int. Cl.
| | | |
|---|---|---|
| *G01N 33/48* | (2006.01) | |
| *G01N 33/50* | (2006.01) | |
| *A61B 5/05* | (2006.01) | |
| *A61B 5/08* | (2006.01) | |
| *A61B 5/024* | (2006.01) | |
| *G01S 7/41* | (2006.01) | |
| *G01S 13/02* | (2006.01) | |
| *G01S 13/56* | (2006.01) | |

(52) U.S. Cl.
CPC ............ *A61B 5/0507* (2013.01); *A61B 5/024* (2013.01); *A61B 5/08* (2013.01); *G01S 7/415* (2013.01); *G01S 13/0209* (2013.01); *G01S 13/56* (2013.01)

(58) Field of Classification Search
None
See application file for complete search history.

(56) References Cited

U.S. PATENT DOCUMENTS

| | | | | |
|---|---|---|---|---|
| 5,959,935 A | * | 9/1999 | Pascucci | G11C 7/22 365/189.09 |
| 6,476,948 B1 | * | 11/2002 | Canal | H04J 3/0682 398/154 |
| 2003/0198303 A1 | * | 10/2003 | Taylor | H04B 1/71057 375/340 |
| 2008/0037795 A1 | * | 2/2008 | Ko | H04S 3/002 381/17 |

FOREIGN PATENT DOCUMENTS

WO WO 2005/092190 A1 * 10/2005

OTHER PUBLICATIONS

Hsieh et al. Respiratory effect on the pulse spectrum. Journal of Medical Engineering & Technology, vol. 27, 2003, pp. 77-84.*
Clifton et al. Measurement of respiratory rate from the photoplethymogram in chest clinic patients. Journal of CLinical Monitoring and Computing, 2006, seven pages.*
Janssens et al. Evaluation of three zero-area digital filters for peak recognition and interference detection in automated spectral data analysis. Analytical Chemistry, 1991, vol. 63, pp. 320-331.*

* cited by examiner

*Primary Examiner* — Russell S Negin
(74) *Attorney, Agent, or Firm* — WPAT, P.C., Intellectual Property Attorneys; Anthony King

(57) ABSTRACT

A pulsed ultra-wideband sensor comprises a control unit designed for forming a time delay of a synchronizing pulse, a probing signal forming path, a transmitting antenna, a receiving antenna, a path of a probing signal transmitter, with an output of said path being connected to the transmitting antenna, a path of a return signal receiver, with an input of the path being connected to the receiving antenna, and a first electronic switch. The input of the first electronic switch is connected to the output of the path for forming a probing signal, and its outputs—to the input of the path of the probing signal transmitter and to the path of a return signal receiver. The outputs of the channels for processing a return signal, which are parts of the path of the return signal receiver, are connected to the path for calculating a respiratory rate and a heart rate.

16 Claims, 14 Drawing Sheets

PULSED ULTRA-WIDEBAND SENSOR AND THE METHOD THEREOF

CROSS REFERENCE TO RELATED APPLICATION

This application claims priority to U.S. Non-Provisional application Ser. No. 12/388,264 filed Feb. 18, 2009 which application is incorporated herein by reference, in its entirety, for any purpose.

BACKGROUND OF THE INVENTION

1. Field of the Invention

The invention relates to the medicinal diagnostic instruments for monitoring individual's physiological parameters, in particular, radar aids for diagnosis of individual's physiological parameters under stationary and field conditions.

2. Description of the Related Art

The employment of ultra-wideband radar as measuring means allows a number of problems to be settled, which may not be realized using traditional diagnostics means. The ultra-wideband sensors allow noninvasive measurements to be taken to thereby avoid the probability of infecting a patient during measurements. In addition, there is no necessity in employing specially furnished laboratories and high-skilled personnel.

The ultra-wideband sensors provide for contact-free diagnosis allowing patients having vast burns or skin diseases to be treated in the absence of the possibility of using contact diagnosis means. With the employment of such sensors, a patient may be investigated through clothing to thereby reduce diagnosis time.

The employment of ultra-wideband sensors provides the desired safety for a patient thanks to the low-level energy of an electromagnetic signal emitted. The radiation load induced to a patient is minimized by orders of magnitude in comparison with X-ray computed tomography.

Moreover, there is no necessity in thorough disinfecting of a measurement instrument and also there is no need in utilizing disposable elements of an apparatus and consumable materials. As a consequence, total expenses for maintaining diagnostic technique are significantly reduced.

According to the classification used nowadays, to the ultra-wideband radar systems may be referred radars with a signal band width determined from the following condition: $0.25 < (f_{upper} - f_{lower})/(f_{upper} + f_{lower}) < 1$, where $f_{upper}$ and $f_{lower}$ are respectively upper and lower boundaries of a signal band width (see, for example, I. Ya. Immoreev. Ultra-wideband radars: new possibilities, unique problems, the features of system. Journal of Bauman's MGTU, Series "Instrument making", Number 4, 1998; I. Ya. Immoreev. The possibilities and features of ultra-wideband radio systems. Applied electronics, Kharkov, vol. 1, No 2, 2002, pages 122 to 140). In addition, the signal bandwidth (($f_{upper} - f_{lower}$) of ultra-wideband radar measurement systems should be at least 500 MHz (see Federal Communications Commission FCC 02-48. D.C. 20554. ET Dockets 98-153. First Report and Order. Apr. 22, 2002). The employment of ultra-wideband radar measurement aids allows the signal information content to be widened owing to an increased distance resolution of the sensor.

Various circuit designs of pulsed ultra-wideband sensors known nowadays are adapted for monitoring the functioning of patient's respiratory organs and a cardio-vascular system. For example, the U.S. Pat. No. 5,519,400 (issued on 21 May 1996) describes a pulsed ultra-wideband sensor with phase-code modulation for controlling the movement of a subject under study. Short video pulses are used as a reference signal and an excitation signal for a transmitting antenna of an apparatus. The apparatus has a signal transmitter with a transmitting antenna sending out an ultra-wideband signal at a frequency of from 2 GHz to 10 GHz. A time delay block generates a control signal determining a time delay between a series of pulse signals. A receiver with a receiving antenna receives discrete signals in accordance with a gating signal of the time delay block. A gating signal delays the receiving of a sent-out pulse signal for a time interval equal to the total time during which the sent-out signal reaches the subject under study and a return signal reaches the receiving antenna. The time delay depends on the distance between the sensor and the subject under study.

A required delay of a probing signal pulses and pulses of a signal to be received is provided by the time delay block. The signals are modulated by means of this block. The modulating signal is encoded in order to avoid the interference of the adjacent radar sensors. The signal receiver comprises a synchronization block for synchronizing with a modulating signal and two quadrature channels for processing a return signal. One of the quadrature channels operates in phase with a reference signal, and in the other channel a signal is generated with a 90° phase shift relative to the reference signal. Data produced from outputs of the quadrature channels of the receiver is used for subsequent analysis of the signals. The quadrature channels are alternately changed-over upon receiving of a return signal by means of a high-speed controllable change-over mechanism. Each of the quadrature channels is equipped with an individual filter and a signal amplifier.

During operation of the prior art radar sensor, the probability of simultaneous processing of the signals delivered to the quadrature channels is excluded. Utilization of a single-channel pattern of processing a return electromagnetic signal in the sensor eliminates the probability of simultaneous processing of the signals in the two quadrature channels in order to neutralize distortions in the received signal.

In turn, the impossibility of joint processing of the signals does not allow data on physiological parameters of the subject under study to be obtained with a desired extent of accuracy at any point on a working distance under measurement process. In this case the so-called "blind" zones occur at the working distance between the sensor and the subject under study, wherein the phase sensitivity of the sensor is significantly decremented in said zones, though the amplitude of the probing signals reflected from the subject may be sufficiently high. The quantity of such zones and the gaps between them depend on an extent of distance under measurement of the radar sensor and a length of oscillation waves filling the probing signal.

The presence of the "blind" zones and the restricted working distance of measurements of the sensor, with the extent of said distance depending on duration of the probing signals, results in degradation of the measurement accuracy of patient's physiological parameters at predetermined points of measurement distance. This imposes essential restrictions on the field of application of the pulsed ultra-wideband sensor. Such a sensor may be used only in case of full immobility of a patient and a fixed distance between the sensor and the patient. Any changing in the position of the patient needs distance retuning of the sensor. In certain cases the position of the sensor relative to the subject under study should be adjusted in order to avoid the occurrence of the patient in the "blind" zone at the measurement distance.

Automatic distance retuning of the sensor is provided through the usage of an automatic distance tracking system which significantly complicates the design of the instrument. However, even the application of the expensive automatic distance tracking system does not eliminate the possibility of occurrence of the subject under study in the "blind" zone.

Another prior art pulsed ultra-wideband sensor used for monitoring the patient's physiological parameters is described in the US published patent application No. 2004/0249258 (issued on 9 Dec. 2004). The instrument is a pulsed ultra-wideband low-power radar with a receiving-transmitting antenna. Short video pulses are used as a reference probing signal. The apparatus comprises a constant-frequency pulse generator, a transmitter, a receiver, a delayed signals generating block, an analog-to-digital signal converter, a signal processing block, a data displaying block, and a control and synchronization block. The signal processing block provides for an expanded statistic processing of return signals. The return signal energy is enhanced by stepped amplification of the signal amplitude in the receiver before the signal is converted to a digital code.

However the given sensor is characterized by the impossibility of avoiding the occurrence of spatial zones where the information content of the return signal is reduced. Moreover, the sensor does not provide for simultaneous generation of reliable data on physiological parameters of patient's various organs.

It is known from the U.S. Pat. No. 5,573,012 (issued on 12 Nov. 1996) a pulsed radar instrument for monitoring various physiological parameters including the parameters of patient's cardio-vascular system and respiratory organs. Functioning of the instrument is based on processing of the signals reflected from the subject under study and generation of a voltage-averaged signal used for modulating a signal of the audio-frequency generator. The signal converter converts the measured voltage of the return signal to an amplitude-frequency modulated audio signal. The apparatus comprises a pulse generator, which generates pulses for opening an input circuit of a signal receiver, and an accumulator for accumulating the receiver input circuit signals.

The received signal may be processed by frequency filtration and amplification for controlling various parameters. However, the signal processing circuit does not rule out the possibility of occurrence of the "blind" zones at the distance between the subject under test and the sensor. Also, the given sensor is not of ultra-wideband type sensors since the frequency of a driving generator is 1 MHz with the signal bandwidth not greater than 0.1 MHz. The return signal is measured and processed in the given sensor using the Doppler effect. Hereupon the sensor does not provide for desired information content of the signal that is intrinsic in the ultra-wideband sensors.

The closest prior art to the claimed invention is a pulsed ultra-wideband sensor for monitoring the parameters of patient's cardio-vascular system and respiratory organs, which is described in the U.S. Pat. No. 4,085,740 (issued on 25 Apr. 1978). The sensor comprises a generator which generates electromagnetic oscillations with a frequency of 10 GHz. The generated signal is modulated with the use of a modulation block. The modulated signal is delivered to a transmitter and is then transferred by means of a transmitting antenna toward the subject under study.

The probing signal reflected from the subject is perceived by a receiving antenna of the sensor and is then branched in two channels of the receiver input circuit. At the same time a probing reference signal is sent out to an attenuator whose output signal is also branched in two channels. The first in-phase reference signal is delivered to a mixer of the first channel of the receiver, and the second reference signal is delivered to a phase-shifting circuit for acquiring a phase shift by an angle of 90°. The output of the phase-shifting circuit is connected to a second input of the mixer of the second channel of the receiver.

The receiver of the sensor has two quadrature channels for processing a return signal. Each of said channels has a signal mixer whose output is connected in series to a detector adapted for signal demodulation. The signal is then supplied to a signal amplifier and a filter. During monitoring of patient's physiological parameters, sine-shaped signals are formed at mixer outputs in the quadrature channels. Upon demodulation of a composite signal of two phase-shifted sinusoids, a signal amplitude is defined as a function of a relative angular phase turning speed of the two signals fed to the mixer input. The magnitude of a relative phase of the return signal in each of the channels describes the frequency of movement of patient's chest or a heart rate depending on tuning of the filters and amplifiers in the signal processing channels.

The first quadrature channel of the receiver is designed for separating a signal indicative of frequency of the chest cyclic motions, and the second quadrature channel is designed for separating the signal indicative of a heart rate. The respective signals are defined using amplifiers and frequency filters tuned for respective amplitude and frequency of patient's physiological parameter under control.

The quadrature channels for processing the return signal in the prior art sensor are of a concrete functional designation. Each of said channels is used for monitoring a certain physiological parameter: a heart rate or a respiratory rate. Due to that, the prior art instrument is characterized by the similar features, as it is with the above instruments, namely: the output signal of the sensor has low information content owing to the presence of "blind" zones at portions of a working measurement distance (in the space between the subject under test and the sensor); the field of application of the sensor is limited due to the necessity of fixing the distance between the sensor and the patient; the sensor may not be used even on a slight movement of the subject under study.

The reduced information content of the return signal results from the processes occurring during diagnosis. The signal carrying useful information is measured in the ultra-wideband sensor by determining the phase difference between the probing reference signal and the signal reflected from the subject under study. Movement of the patient's chest causes changes in the phase incursion of the signal reflected from the subject under test.

The movement of the chest is of reciprocation nature with low amplitude. The maximum chest movement amplitude indicative of normal respiration is 5 mini-meters, whereas the heart beating amplitude is from 0.2 to 2 mini-meters. So, the oscillation frequency of a probing signal must be sufficiently high, from 3 GHz to 20 GHz, in order to enable the desired accuracy in measurements of patient's physiological parameters.

Traditional signal processing patterns characteristic of the above prior art sensors use a correlation system for processing a return signal. The operation of such systems is based on multiplying of a probing signal and a return signal delayed for a time interval during which the signal propagates to the subject under test and comes back to the receiving antenna. Short video pulses with a duration not in the excess of a period of oscillations filling the probing pulse are commonly used as a probing signal. The output signal of the correlation system for processing a return signal is proportional to the phase difference between the probing signal and the return signal.

In case the subject under test is immobile, the amplitude Z of the output signal after processing is determined in compliance with the following correlation:

$$Z = \frac{E_0 E_1}{2} n T_0 \cos(\varphi), \qquad (1)$$

where $E_0$ represents a maximum amplitude of the probing signal;

$E_1$ represents a maximum amplitude of the return signal;
$T_0$ represents a period of oscillations of the probing signal; and
n represents a whole number of periods of oscillations filling the probing pulse.

The magnitude of phase difference φ in the expression (1) is determined by the time during which electromagnetic waves propagate to the subject under test and come back:

$$\varphi = \omega_0 \frac{2R_1}{C} = 4\pi \frac{R_1}{\lambda}, \qquad (2)$$

where $\omega_0 = 2\pi f_0$, representing a circular frequency of the probing signal;

$f_0$ represents an average frequency of the probing signal spectrum;
C represents an electromagnetic wave propagation speed;
λ represents a wavelength of oscillations filling the probing signal; and
$R_1$ represents distance between the subject under test and the sensor.

The normalized chart $Z(R_1)/T_0$ as function of amplitude of an output signal generated by the correlation system for processing a return signal depending on the distance to the subject under test is illustrated in FIG. 1 of the accompanying drawings. As seen from the represented graphical dependence, there are "blind" zones at a working distance between the sensor and the subject under test, wherein the output signal of the sensor is equal to or approximates a zero value. The presence of such zones does not depend on the reflective capacity (an effective scattering area) of the subject under test. The distance between the boundaries of the "blind" zones is proportional to $\lambda/4 = T_0 C/4$ and depends on the probing signal oscillation period.

The number N of such "blind" zones is in reverse proportion to the period $T_0$ of oscillations of the probing signal or the wavelength λ of the probing signal:

$$N = 4\frac{R_1}{T_0 C} = 4\frac{R_1}{\lambda}.$$

The lower is the period (the higher the frequency), the greater number of such zones are created at the working distance of measurement.

In particular, with an average frequency of the probing signal spectrum of 6 GHz at the working distance of 2 meters, there will be 160 of such zones, and the distance between the "blind" zone boundaries will be 12.5 millimeters. It is, therefore, quite probable that during measuring of a respiratory rate and a heart rate, the patient's chest surface which reflects the probing signals will occur within one of the "blind" zones.

In case the subject under test is within the region of the "blind" zone with amplitude of movement of the subject lower than a quarter of the oscillation wavelength of the probing signal, measurements of parameters of subject's movement will be extremely difficult. The indicated circumstances cause an adverse effect upon accuracy of measurement results, which is intolerable in carrying diagnosis of a patient.

With high amplitudes of subject's reciprocating movements, for example, due to patient's deep breath, and high average frequencies of the probing signal spectrum, the shape of the output signal of the correlation system is substantially distorted as compared to the actual function characterizing the movement of the subject under study. It is, therefore, impossible to determine the patient's respiratory rate and heart rate with a desired accuracy.

The amplitude Z(t) of the output signal of a correlation processing system is described by the following expression:

$$Z(t) = E_m \cos(\varphi(t) + \varphi_1), \qquad (3)$$

where $$E_m = \frac{E_0 E_1}{2} n T_0$$

represents a maximum energy of interaction between the return signal and the probing signal, which is released at an output load with a unit resistance;

$$\varphi_1 = 2\omega_0 \frac{R_1}{C} = 4\pi \frac{\Delta R_1}{\lambda}$$

represents a phase shift depended upon the distance between the subject under test and the sensor;

$$\varphi(t) = 2\omega_0 \frac{\Delta R f(\Omega t)}{C} = 4\pi \frac{\Delta R}{\lambda} F(\Omega t)$$

represents an instantaneous phase value resulted from movement of the subject under test;

F(Ωt) represents a law of movement of the subject under test;
Ω=2πf which represents a circular frequency of reciprocation of the subject under test;
f represents a frequency of reciprocation of the subject under test;
t represents a current time;
ΔR represents a maximum amplitude of movement of the subject under test.

Suppose the subject under study is at a distance $R_1$ from the sensor and is movable in accordance with a sinusoidal law at a circular frequency Ω and amplitude ΔR. Such expression (3) for the output signal will assume the following form:

$$Z(t) = E_m \cos\left(4\pi \frac{\Delta R}{\lambda} \sin(\Omega t) + 4\pi \frac{R_1}{\lambda}\right), \qquad (4)$$

Oscillograms of the output signal (changing in the amplitude $Z(t)$ and the amplitude-and-frequency spectrum $Z(f_1)$ of the output signal) of the correlation system are illustrated in FIGS. 2 to 9 on the accompanying drawings. The changed amplitude $Z(t)$ of the signal in the represented charts has only a variable component. The cited curves refer to the various values m (m=0.5 in FIGS. 2 and 3; m=2 in FIGS. 4 and 5; m=5 in FIGS. 6 and 7; m=10 in FIGS. 8 and 9), said values being determined in compliance with the ratio of $$m = 4\pi \frac{\Delta R}{\pi}.$$

The curves show the nature of changing in the output signal with varying values $\Delta R$ of the oscillations amplitude of the subject under study and respective values m. The measured oscillation frequency of the subject under test was 1 Hz. The value $f_1$ in the charts is the frequency of the signal reflected from the subject under test.

It follows from the curves that the shape of the output signal essentially differs from the real law of movement of the subject with greater values $\Delta R$ in comparison with the wavelength $\lambda$. With $\Delta R > \lambda$ (see FIGS. 4 to 9, m=2, 5 and 10), the function of changing the amplitude and movement speed of the subject under study becomes difficult to be determined in case a single-channel signal processing circuit is used.

With low values of oscillations amplitude $\Delta R$ of the subject under study in comparison with the wavelength $\lambda$ ($\Delta R < \lambda$), the output signal of the quadrature channel may have variable as well as constant components. It should be noted that the constant component of the return signal contains useful information on immobile subjects, the subject under test also being among said immobile subjects. In the prior art apparatuses such constant signal components are removed by filters in each channel for processing a return signal before the subsequent programmed processing of the signal. Therefore, useful information needed for enabling an accurate determination of physiological parameters is loosed.

A special programmed signal calibration for the immovable subject under test is used for the purpose of recovering the information on movement of the subject under study, said information being contained in the constant component of the return signal. In case the position of the subject under study is changed, the signal calibration procedure should be repeated. This leads to prolonged measurements and complicated software and design of the sensor.

SUMMARY OF THE INVENTION

The claimed invention is targeted at elimination of the above intrinsic in the prior art apparatuses and including the impossibility of simultaneous processing of the signal reflected from the subject under study in the two processing channels and separation of a maximum information-saturated part of the return signal for further processing and determining the patient's heart rate, respiratory rate or other physiological parameters at a desired accuracy.

The claimed invention provides a novel technical result to resolve the given technical problem, and the technical result includes an increase in the phase sensitivity of the sensor and a precise determination of a heart rate, a respiratory rate or other physiological parameters upon movement of the patient within a range of working distances of measurements.

The achievement of the given technical result is provided through the usage of a pulsed ultra-wideband sensor. The sensor comprises a control unit adapted for forming a time delay of synchronizing pulse, a probing signal forming path including a coherent radio pulse generator connected to the control unit, a transmitting antenna, a receiving antenna, a probing signal transmitter path, whose output is connected to the transmitting antenna, and a return signal receiver path comprising two quadrature channels for processing of a return signal. Each of said channels comprises a signal mixer having a first input connected to the receiving antenna, and a phase-shifting circuit whose input is connected to an output of the probing signal forming path. The output of the phase-shifting circuit is connected to a second input of the signal mixer of the second channel for processing a return signal.

The sensor implemented according to the given invention comprises a first electronic switch, a respiratory rate and heart rate calculating path including two frequency filters, two adders, two signal amplitude calculating blocks, two signal energy calculating blocks, two integrators, two comparators, two signal multiplying blocks, two block for generating reference signals, a second electronic switch and a third electronic switch, a respiratory rate calculating block, and a heart rate calculating block.

The input of the first electronic switch is connected to the output of the probing signal forming path. The first output of the first electronic switch is connected to the input of the path of the probing signal transmitter. The second output of the first electronic switch is connected to the second input of the signal mixer of the first channel for processing a return signal and to the input of the phase-shifting circuit. The control input of the first electronic switch is connected to the control unit.

The inputs of the first and second frequency filters are connected respectively to the outputs of the first and second channels for processing a return signal. The first input of the first adder is connected to the output of the first channel for processing a return signal. The second input of the first adder is connected to the output of the first frequency filter. The first input of the second adder is connected to the output of the second channel for processing a return signal. The second input of the second adder is connected to the output of the second frequency filter.

The first input of the first signal multiplying block is connected to the output of the first adder. The second input of the first signal multiplying block is connected to the output of the first block for generating a reference signal. The first input of the second signal multiplying block is connected to the output of the second adder. The second input of the second signal multiplying block is connected to the output of the second block for generating a reference signal.

The input of the first integrator is connected to the output of the first signal multiplying block. The output of the first integrator is connected to the first input of the second electronic switch and to the input of the first signal energy calculating block. The input of the second integrator is connected to the output of the second signal multiplying block. The output of the second integrator is connected to the second input of the second electronic switch and to the input of the second signal energy calculating block. The output of the first signal energy calculating block is connected to the first input of the first comparator. The output of the second signal energy calculating block is connected to the second input of the first comparator. The output of the first comparator is connected to the control input of the second electronic switch.

The input of the first signal amplitude calculating block is connected to the output of the first frequency filter. The output of first signal amplitude calculating block is connected to the first input of the second comparator. The input of the second signal amplitude calculating block is connected to the output of the second frequency filter. The output of the second signal amplitude calculating block is connected to the second input of the second comparator. The output of the second comparator is connected to the control input of the third electronic switch, whose first input is connected to the output of the first frequency filter and second input is connected to the output of the second frequency filter. The output of the third switch is connected to the input of the respiratory rate calculating block, and the output of the second electronic switch is connected to the input of the heart rate calculating block.

The method for measuring physiological parameters according to the embodiments of the invention comprises: filtering a first information signal and a second information signal indicative of both a first and a second physiological parameters to generate a first filtered signal and a second filtered signal indicative of merely a first physiological parameter; subtracting, from the first information signal, the first filtered signal to generate a first subtracted signal indicative of merely a second physiological parameter; subtracting, from the second information signal, the second filtered signal to generate a second subtracted signal indicative of merely a second physiological parameter; correlating the first subtracted signal with a first reference signal to generate a first correlated signal; correlating the second subtracted signal with a second reference signal to generate a second correlated signal; selecting a first physiological parameter signal from the first filtered signal and the second filtered signal based on the amplitudes of the first filtered signal and the second filtered signal; and selecting a second physiological parameter from the first correlated signal and the second correlated signal based on the energies of the first filtered signal and the second filtered signal.

The invention is exemplified by the description of concrete examples of embodiment of the pulsed ultra-wideband sensor designed for measuring a respiratory rate, a heart rate or other physiological parameters and the method thereof.

EMBODIMENT OF THE PRESENT INVENTION

Figure 1:
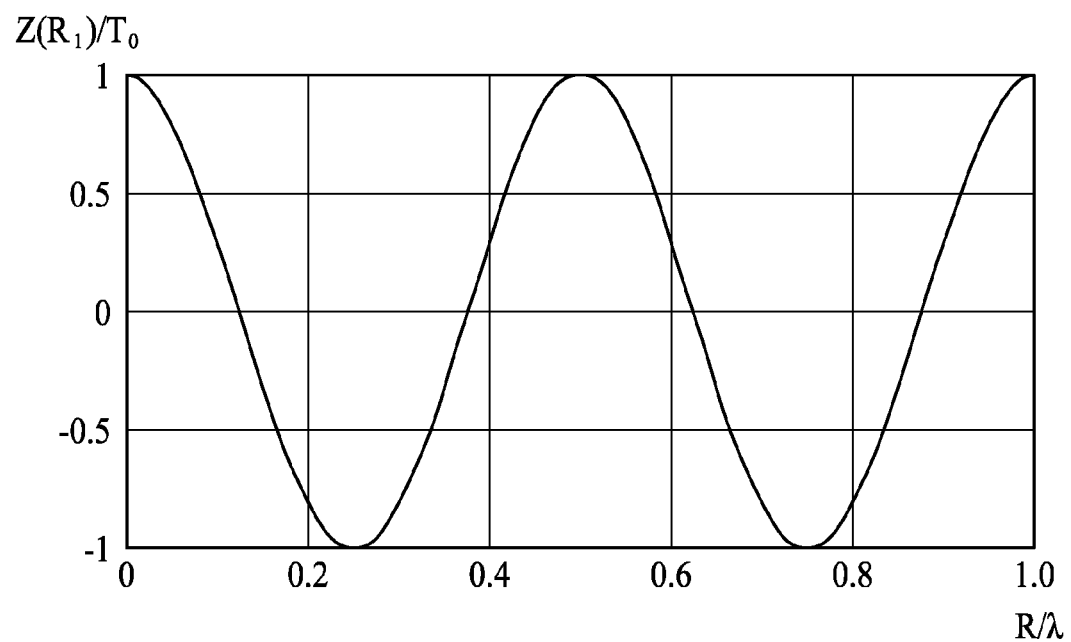
FIG. 1 is a normalized chart $Z(R_1)/T_0$ of an output signal of a correlation processing system depending on a relative distance $R_1/\lambda$ to the immobile subject under study.
Figure 2:
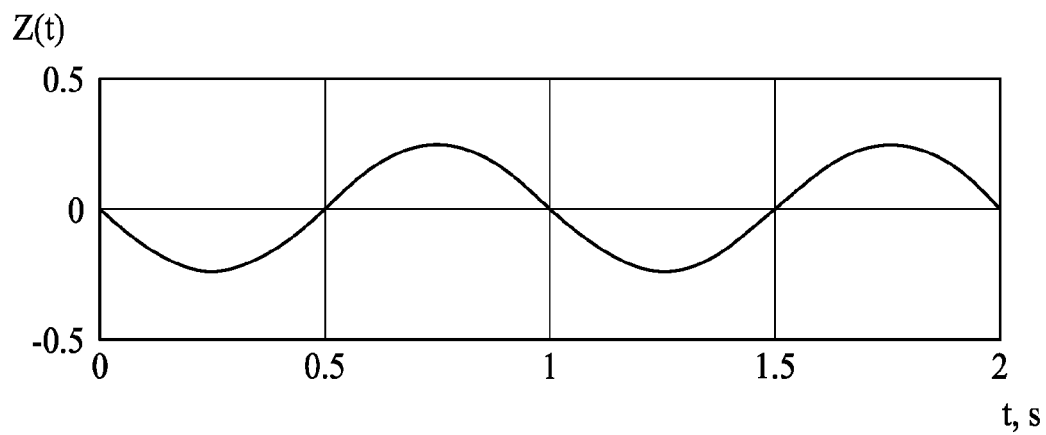
FIG. 2 is a chart of function $Z(t)$ of an output signal of a correlation processing system with m=0.5.
Figure 3:
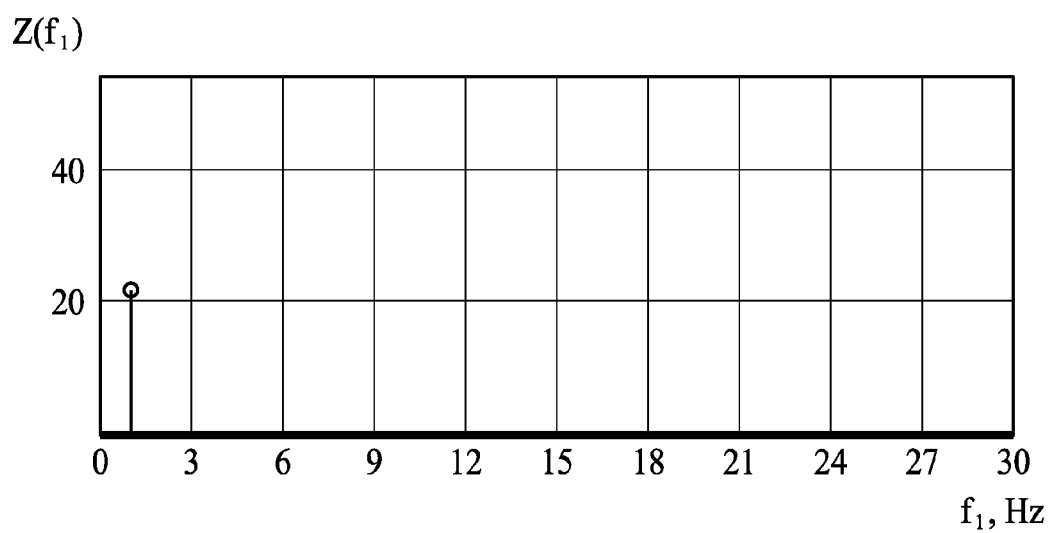
FIG. 3 is an amplitude-frequency spectrum $Z(f_1)$ of an output signal of a correlation processing system with m=0.5.
Figure 4:
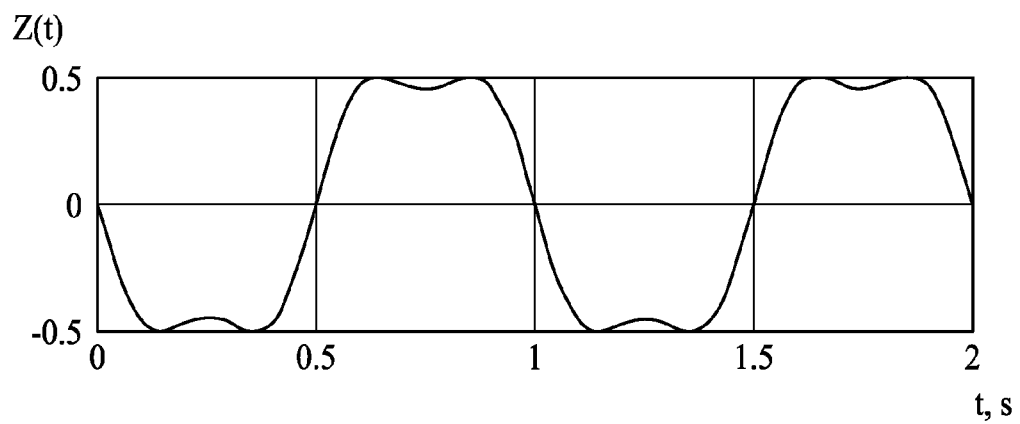
FIG. 4 is a chart of function $Z(t)$ of an output signal of a correlation processing system with m=2.
Figure 5:
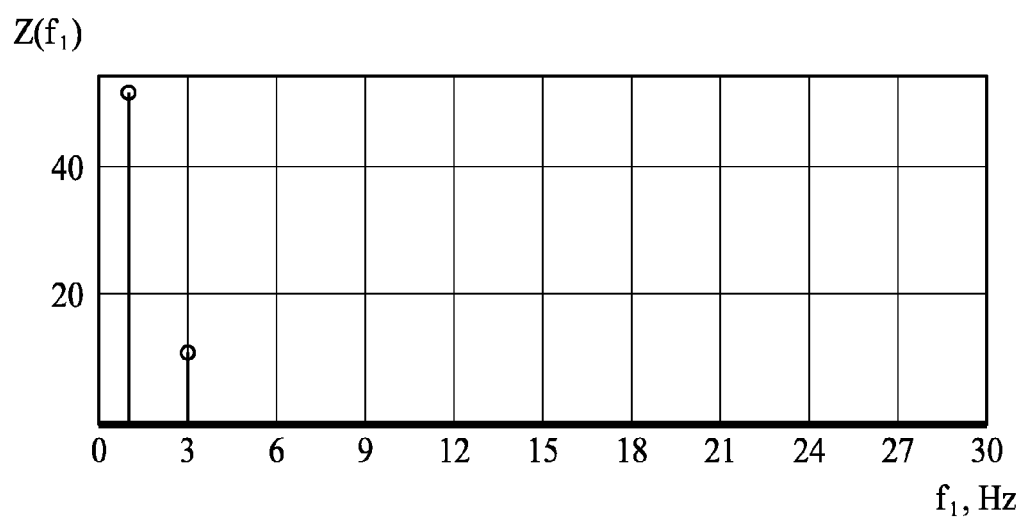
FIG. 5 is an amplitude-frequency spectrum $Z(f_1)$ of an output signal of a correlation processing system with m=2.
Figure 6:
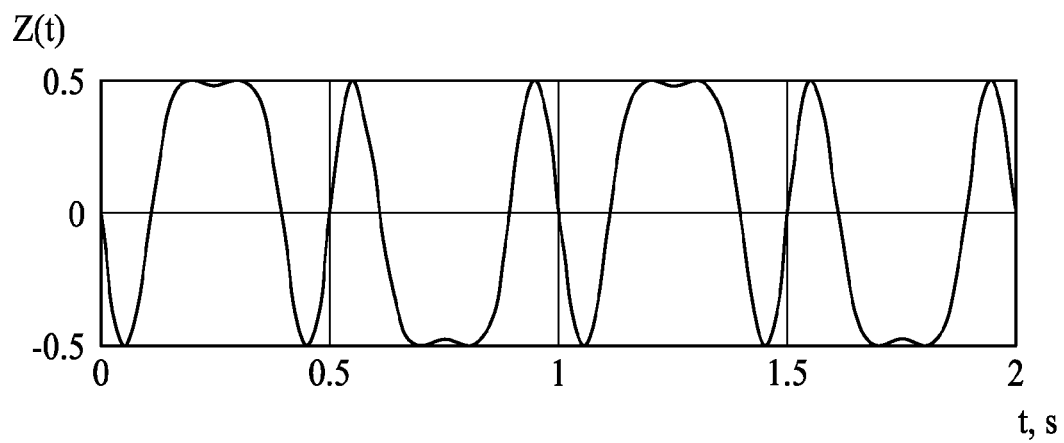
FIG. 6 is a chart of function $Z(t)$ of an output signal of a correlation processing system with m=5.
Figure 7:
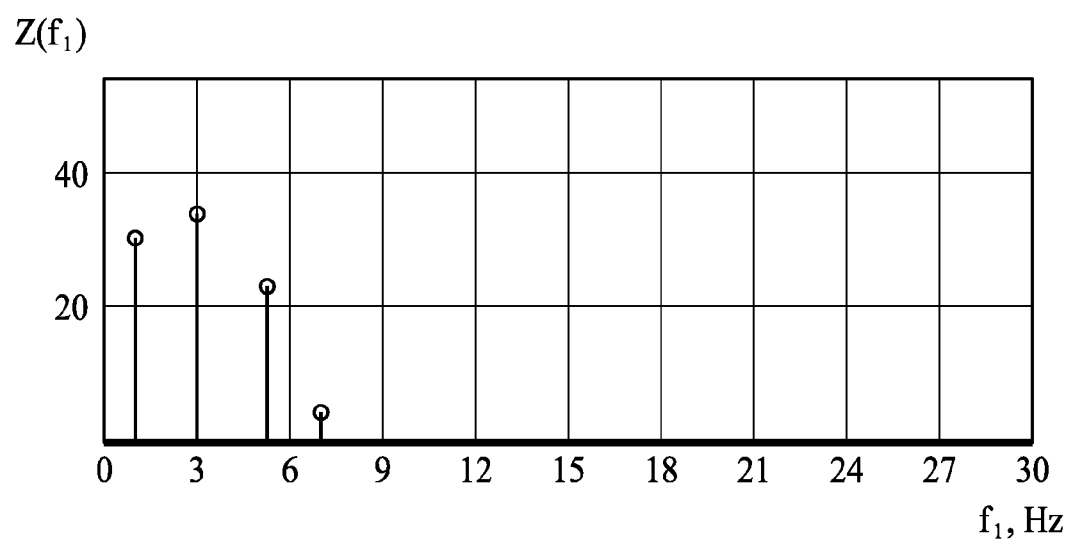
FIG. 7 is an amplitude-frequency spectrum $Z(f_1)$ of an output signal of a correlation processing system with m=5.
Figure 8:
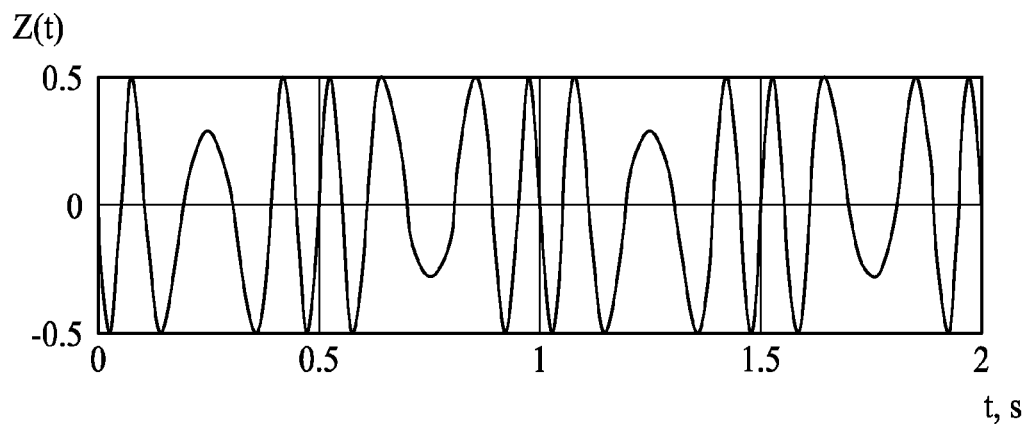
FIG. 8 is a chart of function $Z(t)$ of an output signal of a correlation processing system with m=10.
Figure 9:
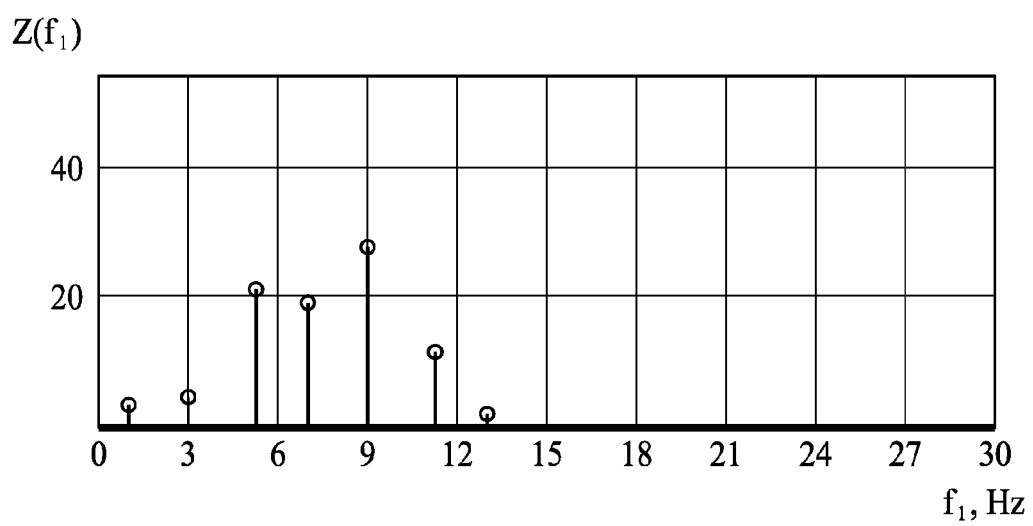
FIG. 9 is an amplitude-frequency spectrum $Z(f_1)$ of an output signal of a correlation processing system with m=10.
Figure 10:
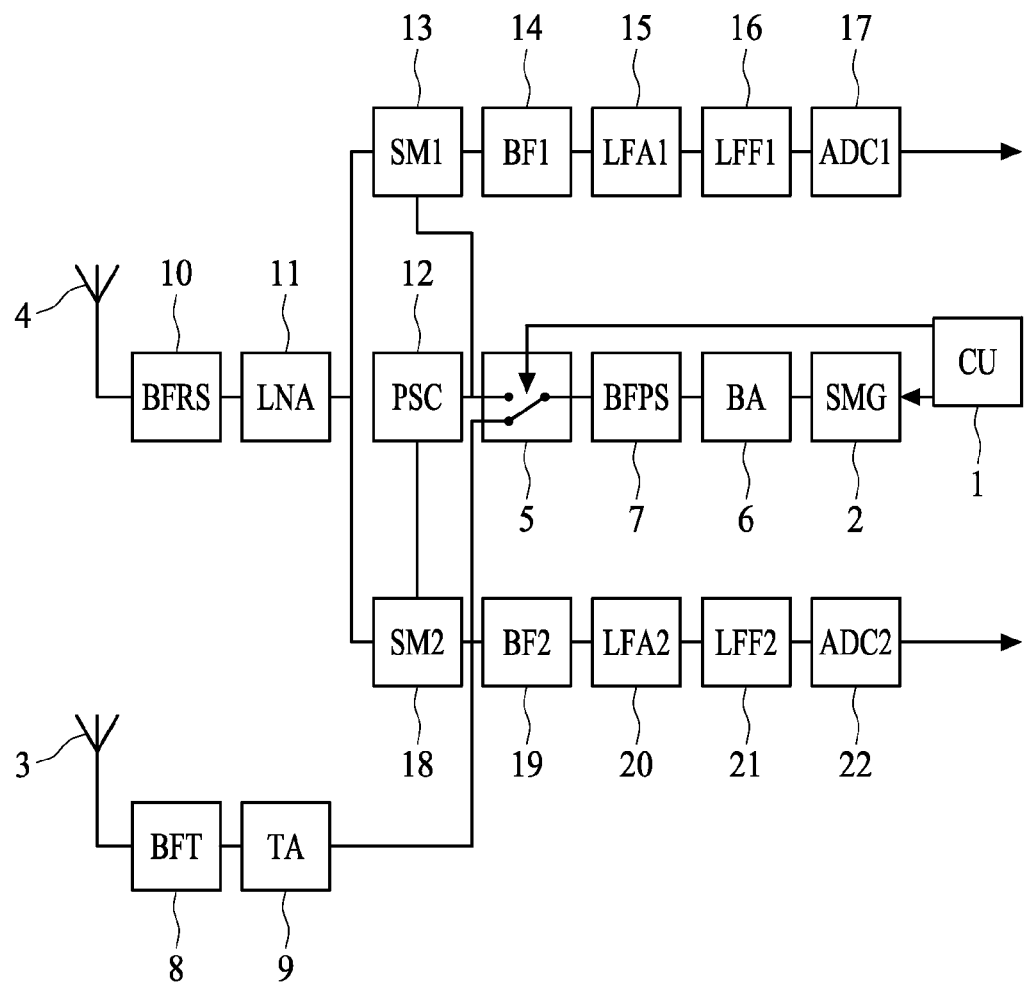
FIG. 10 is a block diagram of a probing signal forming path, a path of a probing signal transmitter, and a path of a return signal receiver.

The pulsed ultra-wideband sensor comprises a control unit 1 (CU) for forming a time delay for a synchronizing signal, a probing signal forming path including an externally excited self-contained microwave generator (SMG) 2 used as a coherent radio pulse generator (see FIG. 10). The sensor is further provided with a transmitting antenna 3 and a receiving antenna 4, a path of a probing signal transmitter, a first electronic switch 5, and a path of a return signal receiver with two channels for processing a return signal (see FIG. 10).

The probing signal forming path comprises a buffer amplifier 6 (BA) and a band pass filter 7 (BFPS) for the probing signal, which are connected in series with the self-contained microwave generator 2. The band pass filter 7 is connected to the input of the first electronic switch 5. The path of the probing signal transmitter comprises a band pass filter 8 (BFT) of the transmitter and an amplifier 9 (TA) of the transmitter, which are connected in series to the transmitting antenna 3, with the input of amplifier being connected to the first output of the controlled electronic switch 5 (see FIG. 10).

The path of the return signal receiver comprises a band pass filter 10 (BFRS) for the return signal and a low-noise amplifier 11 (LNA), which are connected in series to the receiving antenna 4, with the output of the low-noise amplifier being connected to the two parallel switched channels for processing a return signal. The receiver path also includes a phase-shifting circuit 12 (PSC). The first channel for processing a return signal comprises a signal mixer 13 (SM1) to the output of which signal mixer are connected in series a band pass filter 14 (BF1), a low-frequency amplifier 15 (LFA1), a low-frequency filter 16 (LFF1), and an analog-to-digital converter 17 (ADC1). The first input of the signal mixer 13 is connected to the output of the low-noise amplifier 11 while the second input is connected to the second output of the first electronic switch 5 (see FIG. 10).

The second channel for processing a return signal comprises a signal mixer 18 (SM2) to the output of which mixer are connected in series a band pass filter 19 (BF2), a low-frequency amplifier 20 (LFA2), a low-frequency filter 21 (LFF2) and an analog-to-digital converter 22 (ADC2). The first input of the signal mixer 18 is connected to the output of the low-noise amplifier 11 while the second input is connected to the second output of the first electronic switch 5 through the phase-shifting circuit 12 providing a phase shift of a probing signal by an angle of 90°. The low-frequency filters 16 and 21 with a lower frequency boundary of about 0.1 Hz provide for selection of the signals under process with a band pass higher than the indicated "cutoff frequency" (see FIG. 10).

Figure 11:
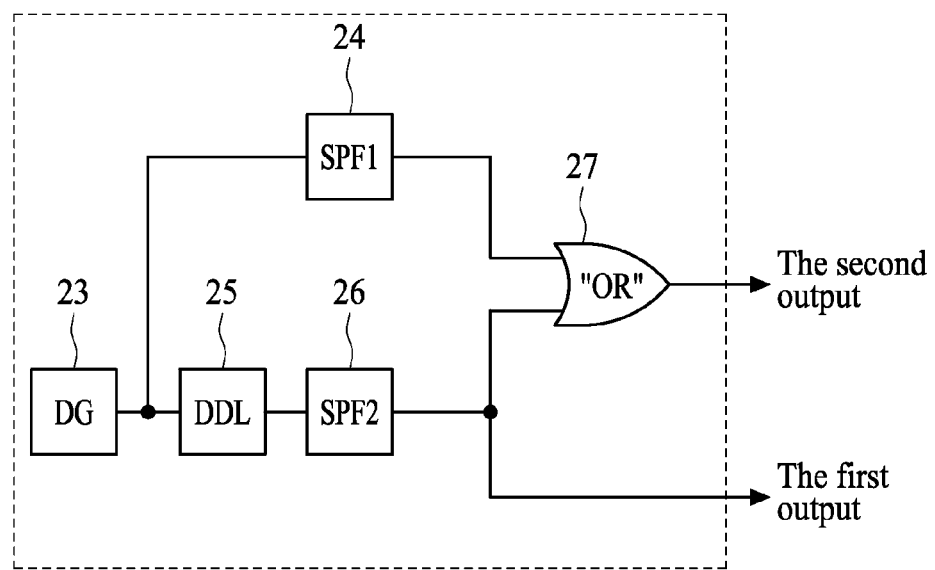
FIG. 11 is a block diagram of a control unit.

The control unit 1 for forming a time delay for a synchronizing pulse, whose block diagram is shown in FIG. 11, comprises a driving generator 23 (DG), a path for forming a synchronizing signal of the transmitter and controlling the process of forming a probing signal, and a path for forming a synchronizing signal of the receiver.

The path for forming a synchronizing signal of the transmitter comprises a first short-pulse former 24 (SPF1) by means of which a short video pulse of the synchronizing signal is generated. The path for forming a synchronizing signal of the receiver, consisting of a controlled digital delay line 25 (DDL) and a second short-pulse former 26 (SPF2), defines a first output of the control unit 1, said output being connected to a control input of the first electronic switch 5. Both paths for forming synchronizing signals of the transmitter and the receiver are connected to the inputs of an "OR" circuit 27 whose output forms a second output of the control unit 1. This output is connected to the control input of the self-contained microwave generator 2 (see FIG. 11).

Figure 12:
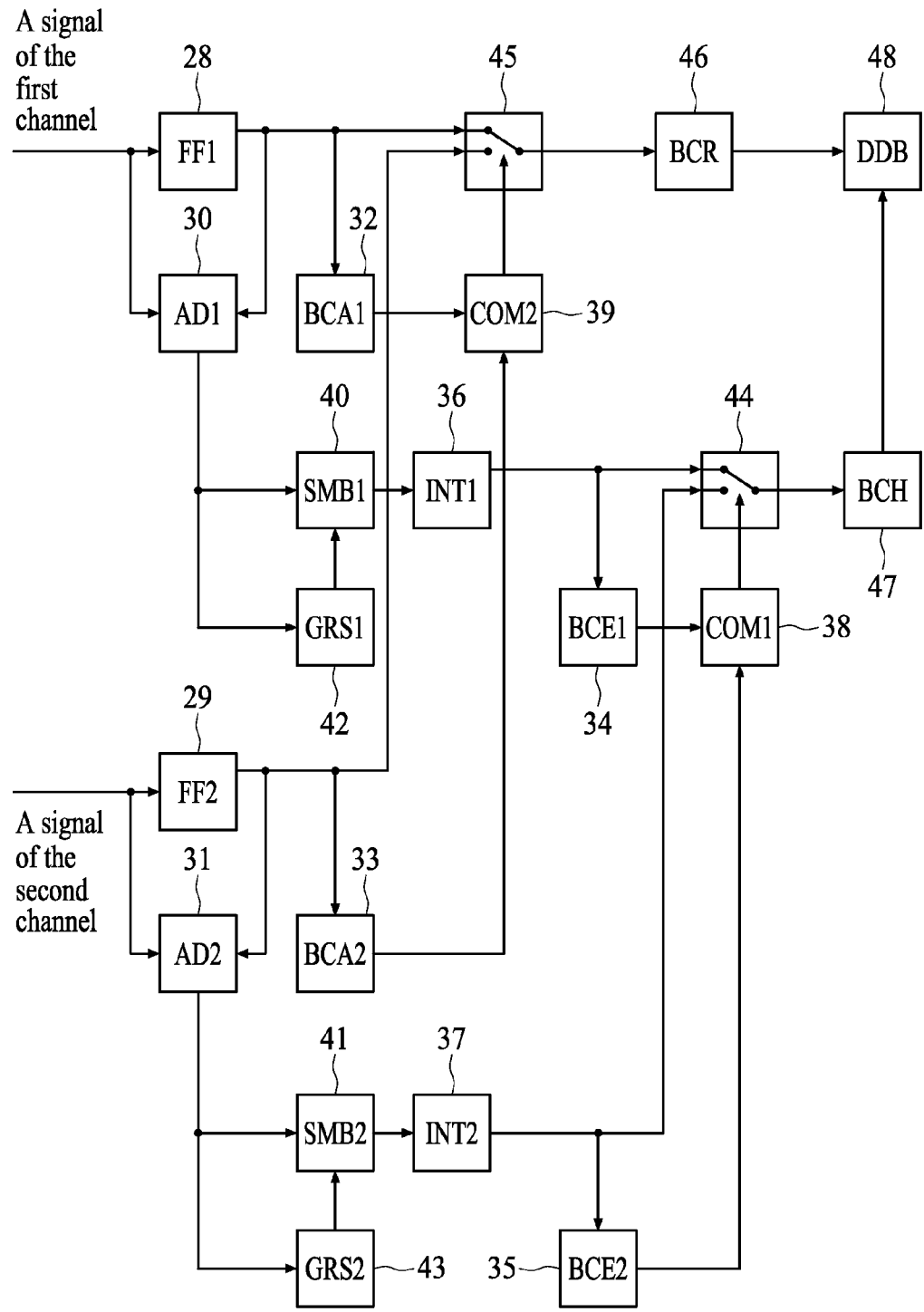
FIG. 12 is a block diagram of a respiratory rate and heart rate calculating path in the first version of embodiment.
Figure 13:
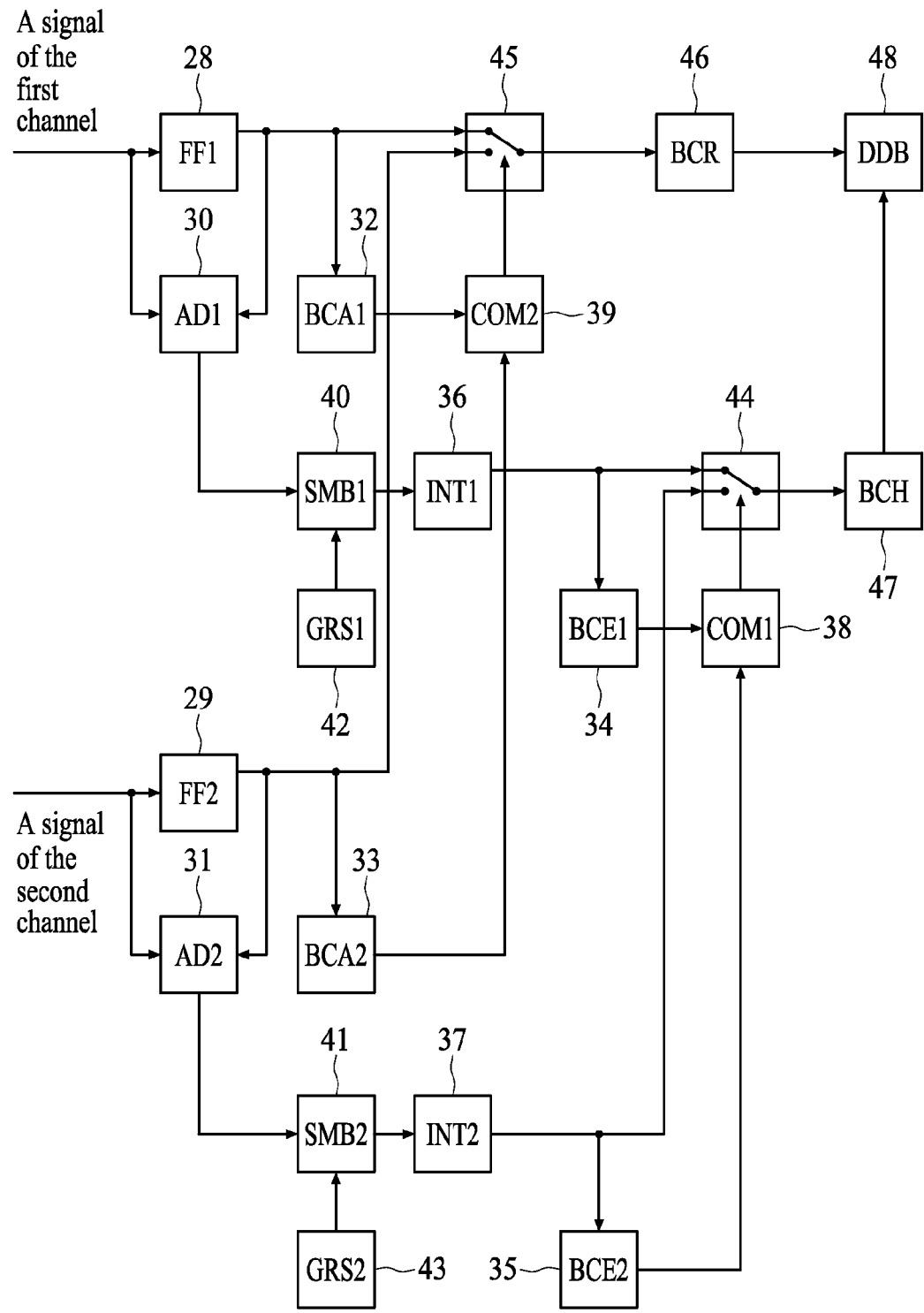
FIG. 13 is a block diagram of a respiratory rate and heart rate calculating path in the second version of embodiment.

The respiratory and heart rates calculating path whose block diagram is shown in FIGS. 12 and 13 includes two frequency filters 28 and 29 (FF1 and FF2), two adders 30 and 31 (AD1 and AD2), two blocks 32 and 33 (BCA1 and BCA2) for calculating signal amplitude, two blocks 34 and 35 (BCE1 and BCE2) for calculating signal energy, two integrators 36 and 37 (INT1 and INT2), two comparators 38 and 39 (COM1 and COM2), two signal multiplying blocks 40 and 41 (SMB1 and SMB2), two blocks 42 and 43 (GRS1 and GRS2) for generating reference signals, a second electronic switch 44 and a third electronic switch 45, a respiratory rate calculating block 46 (BCR), a heart rate calculating block 47 (BCH), and a data displaying block 48 (DDB).

The frequency filters 28 and 29 are designed for frequency selection of the signals defining a movement of a chest and the signals defining heartbeats. The given signals are contained in a return signal which is an integral curve of a patient's respiration and heartbeat function. The frequency filters 28 and 29 have a band pass providing "smoothing" of the frequencies characteristic of the heart rate on the integral curve of the return signal. The said curve includes the frequency characteristics of the chest oscillations and heart beats. The band pass of the filters 28 and 29 is delimited by an upper "cutoff frequency" of about 1 Hz.

The input of the first frequency filter 28 is connected to the output of the first channel for processing a return signal. The input of the second frequency filter 29 is connected to the output of the second channel for processing a return signal. In an embodiment, the inputs of the first and second frequency filters 28 and 29 are connected to the outputs of the analog-to-digital converters 17 and 22, respectively.

The first input of the first adder 30 is connected to the output of the first channel for processing a return signal, with the output of the analog-to-digital converter 17 serving as an output of said first channel. The second input of the first adder 30 is connected to the output of the first frequency filter 28. The first input of the second adder 31 is connected to the output of the second channel for processing a return signal, with the output of the analog-to-digital converter 22 serving as an output of said second channel. The second input of the second adder 31 is connected to the output of the second frequency filter 29.

The first input of the first signal multiplying block 40 is connected to the output of the first adder 30. The second input of the first signal multiplying block 40 is connected to the output of the first block 42 for generating a reference signal. The first input of the second signal multiplying block 41 is connected to the output of the second adder 31. The second input of the second signal multiplying block 41 is connected to the output of the second block 43 for generating a reference signal.

The input of the first integrator 36 is connected to the output of the first signal multiplying block 40. The output of the first integrator 36 is connected to the first input of the second electronic switch 44 and to the input of the first block 34 for calculating signal energy. The input of the second integrator 37 is connected to the output of the second signal multiplying block 41. The output of the second integrator 37 is connected to the second input of the second electronic switch 44 and to the input of the second block 35 for calculating signal energy.

The output of the first block 34 for calculating signal energy is connected to the first input of the first comparator 38. The output of the second block 35 for calculating signal energy is connected to the second input of the first comparator 38. The output of the first comparator 38 is connected to the control input of the second electronic switch 44.

The input of the first block 32 for calculating signal amplitude is connected to the output of the first frequency filter 28. The output of the first block 32 for calculating signal amplitude is connected to the first input of the second comparator 39. The input of the second block 33 for calculating signal amplitude is connected to the output of the second frequency filter 29. The output of second block 33 for calculating signal amplitude is connected to the second input of the second comparator 39. The output of the second comparator 39 is connected to the control input of the third electronic switch 45.

The first input of the third electronic switch 45 is connected to the output of the first frequency filter 28, and the second input—to the output of the second frequency filter 29. The output of the third electronic switch 45 is connected to the input of the respiratory rate calculating block 46. The output of the second electronic switch 44 is connected to the input of the heart rate calculating block 47. The first input of the data displaying block 48 is connected to the output of the heart rate calculating block 47. The second input of the data displaying block 48 is connected to the output of the respiratory rate calculating block 46.

In the first version of embodiment of the path for calculating respiratory and heat rates, illustrated in FIG. 12, the blocks 42 and 43 for generating reference signals are provided with inputs connected to the outputs of the adders 30 and 31, respectively. The output signals of the adders 30 and 31 in the given version of embodiment are used for forming a reference signal in the form of lengths of a return signal under process in real time. Duration of time intervals for such signal lengths is selected to be 3 seconds. The formed reference signals are transferred to the input of the respective signal multiplying block (40 or 41).

In the second version of embodiment of the respiratory and heart rates calculating path illustrated in FIG. 13, the blocks 42 and 43 for generating reference signals are designed for forming signals of constant shape. The reference signal is introduced into a memory element of each of said blocks 42 and 43 for generating reference signals and transferred to the input of the respective signal multiplying block (40 or 41). The reference signal may be a signal length with duration of 3 seconds, said signal length being characterized by the following dependence:

$$Z(t) = -(t^2 - 1) \times \exp\left(-\frac{t^2}{2}\right)$$

It should be noted that in an embodiment, a number of additional elements and blocks are used which may be avoided, under the stipulation that the implementation of the invention and the achievement of the technical result connected with an increase in a phase sensitivity of the sensor and an accuracy of measurements upon movement of the subject under study may be still reached.

Particularly, in certain cases of a constructive embodiment of the sensor, the employment of a common data displaying block is not needed. The outputs of the signal mixers 13 and 18 functioning in the sensor as phase detectors may be directly connected to the inputs of the frequency filters 28 and 29. The channels for processing the return signal may be connected to the receiving antenna 4 without usage of additional means for signal amplification and frequency selection. In the path of the probing signal transmitter, the transmitting antenna 3 may be connected directly to the first output of the first electronic switch 5.

Moreover, in some versions of constructive embodiment of the sensor, the transmitting antenna 3 and the receiving antenna 4 may be integrated in a single block of the transmit-receive device (not shown in the drawing). The given block provides coupling at various periods of time of the transmit-receive device, which alternately functions as an electromagnetic signal emitter and receiver, to the path of the probing signal transmitter in the operation of the transmitting antenna; or to the path of the return signal receiver in the operation of the receiving antenna. The paths of the transmitter and the receiver may be alternately coupled to the block of the transmitting-and-receiving antenna through an additional electronic switch. The employment of the single block of the transmitting-and-receiving antenna enables integration of two independently functioning antennas in a single constructional part of the sensor.

The above described pulsed ultra-wideband sensor operates as follows.

Figure 14:
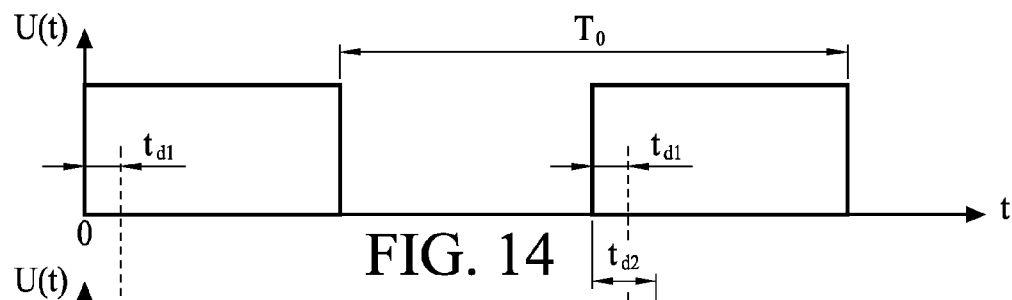
FIG. 14 is a time diagram $U(t)$ of synchronizing pulses at the output of a driving generator of a control unit.

The driving generator 23 generates square-shaped synchronizing pulses with a period $T_0$ (a time diagram of synchronizing pulses is represented in FIG. 14). Then the signal is divided and received into two paths: the path for forming a synchronizing signal of the transmitter designed for controlling the generation of a probing signal, and the path for forming a synchronizing signal of the receiver.

Figure 16:
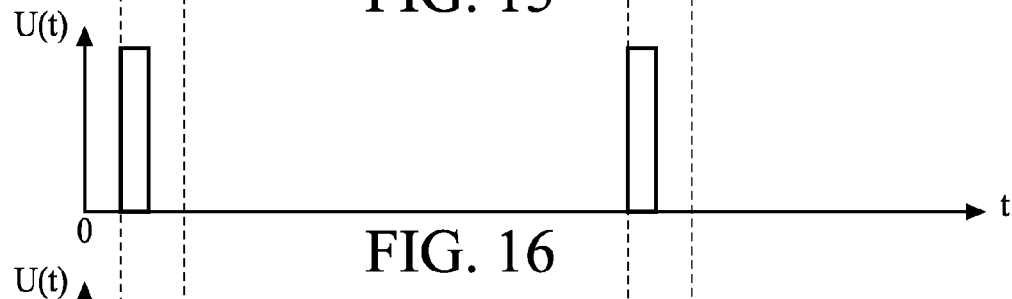
FIG. 16 is a time diagram $U(t)$ of synchronizing pulses at the output of a first short pulse generating element of a synchronizing signal forming path of the transmitter.

In the path for forming a synchronizing signal of the transmitter, a short video pulse with a delay $t_{d1}$ (see FIG. 16) is formed at the leading edge of the first synchronizing pulse by means of a first short-pulse former 24. The duration of the formed pulse depends on the desired duration of the probing signal.

Figure 15:
FIG. 15 is a time diagram $U(t)$ of synchronizing pulses at the output of a delay line of a synchronizing signal forming path of the receiver.
Figure 17:
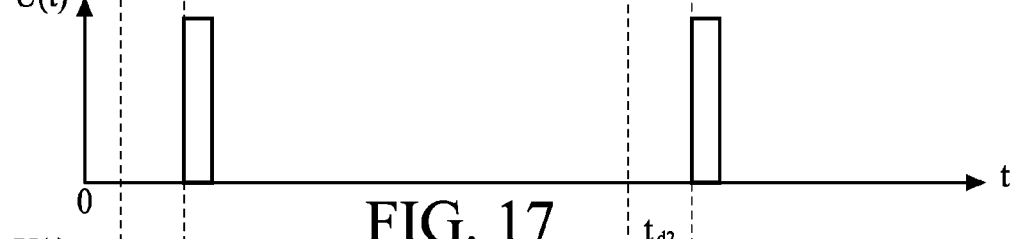
FIG. 17 is a time diagram $U(t)$ of synchronizing pulses at the output of a second short pulse generating element of a synchronizing signal forming path of the receiver.

In the path for forming a synchronizing signal of the receiver, the controlled digital delay line 25 provides delaying of the synchronizing pulse for a time $t_{d2}$ (see the time diagram in FIG. 15) during which delay the probing signal is propagated to the subject under test and comes back to the sensor. The delay value defines the extent of the working distance of measurement of the sensor and is calculated according to the formula:

$$t_{d2} = \frac{2R_1}{C},$$

where $R_1$ represents a distance between the subject under study and the sensor, and C represents a propagation speed of electromagnetic waves. Using the second short-pulse former 26, a short video pulse of a synchronizing signal with a delay of $t_{d3}=t_{d1}$ (see FIG. 17) is formed at the leading edge of the second synchronizing pulse. The given synchronizing signal is sent to the first output of the control unit 1 connected to the control input of the first electronic switch 5.

Figure 18:
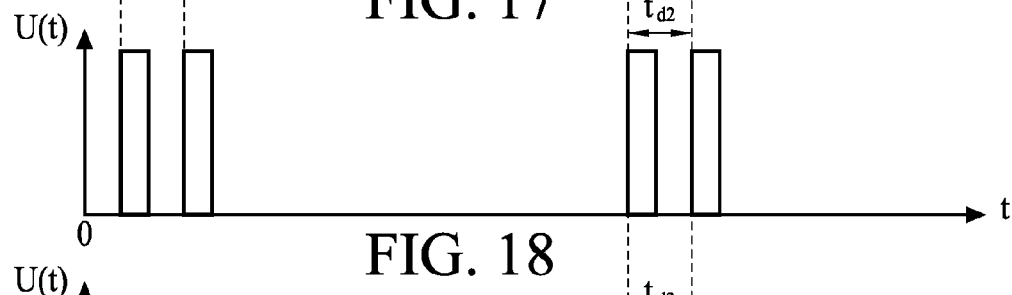
FIG. 18 is a time diagram $U(t)$ of synchronizing pulses at the output of a control unit.
Figure 19:
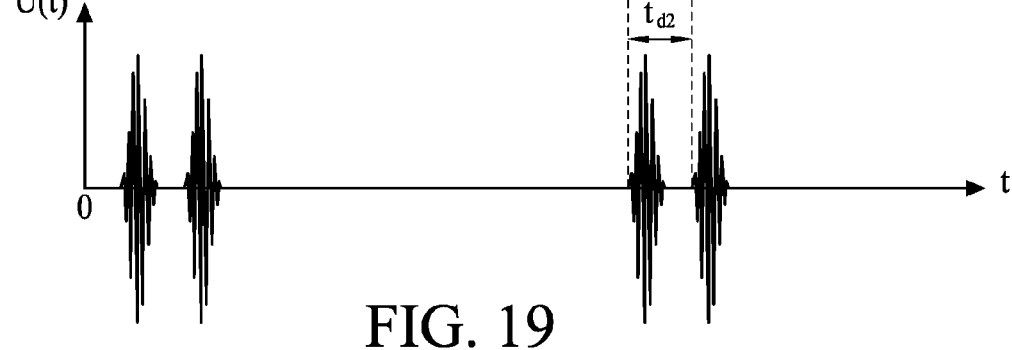
FIG. 19 is a time diagram $U(t)$ of coherent radio pulses at the output of a self-contained microwave generator.

The synchronizing signals formed in the paths of the control unit by means of the "OR" circuit 27 are combined into a single synchronizing signal which is a periodic sequence of pairs of video pulses-duplets (see FIG. 18). The time interval between the duplet pulses is defined by the delay time $t_{d2}$. The period $T_0$ of duplet pulses is set by the driving generator 23. The synchronizing signal including the duplet of video pulses is sent to the second output of the control unit 1 connected to the control input of the self-contained microwave generator 2. On entry of the control synchronizing signal, the self-contained microwave generator 2 generates two coherent radio pulses following each other with a time interval $t_{d2}$ (see FIG. 19).

The duplet of coherent pulses formed in the self-contained microwave generator 2 is transmitted through a buffer amplifier 6 and a band pass filter 7 of the probing signal to the input of the first electronic switch 5. The first electronic switch 5 is controlled by means of synchronizing signals delivered from the first output of the control unit 1 to the control input of the electronic switch. The first electronic switch 5 provides for controlled switching of the signals formed in the probing signal forming path. Controlled by the synchronizing signals of the control unit 1, the probing signals are sent to the path of the signal transmitter or to the path of the return signal receiver.

In the initial state, the first electronic switch 5 is in the position shown in FIG. 10. In the given position, the signal of the self-contained microwave generator 2 enters the path of the probing signal transmitter. In the amplifier of the transmitter 9 the probing signal is amplified to the desired extent. The band pass filters 7, 8 and 10 have a pass band of from 3 GHz to 10 GHz and are designed for suppressing the out-of-band radiation.

The generated probing signal is transmitted to the transmitting antenna 3 and spread toward the subject under study. In a rated time interval $t_{d2}$ necessary for propagation of the probing signal to the subject under test and back to the sensor, a video pulse is generated in the path for forming a synchronizing signal of the receiver, said video pulse being transferred from the first output of the control unit 1 to the control input of the first electronic switch 5.

On entry of the synchronizing signal, a controlling action is generated in the first electronic switch for changing the switching of contacts. As a result, the probing signal forming path is connected to the second inputs of the signal mixers 13 and 18. The probing reference signal is delivered to the signal mixer 18 after passage through the phase-shifting circuit 12 providing a phase shift by an angle of 90°. As a result, the second coherent radio pulse of the self-contained microwave generator 2 enters the second channel for processing a return signal with a shifted phase. The in-phase signal and the signal with a shifted phase function are served as reference signals for the signal mixers 13 and 18.

The signal reflected from the subject under test and received by the receiving antenna 4 passes through the band pass filter 10 of the return signal, providing reduction in the level of noises from the outside radio systems, and is amplified to the desired extent by means of the low-noise amplifier 11. The filtered out and amplified return signal is sent to the channels for processing a return signal at the first inputs of the signal mixers 13 and 18 functioning as phase detectors. After correlation with the probing reference signals which are sent to the second inputs of the signal mixers 13 and 18, two signals are generated in the channels for processing a return signal: a first in-phase signal in the first channel and a second signal with a phase shift by an angle of 90° in the second channel.

In each of the channels for processing a return signal, the signal is separated in each of the band pass filters 14 and 19 and the signals are amplified by means of the low-frequency amplifiers 15 and 20. The low-frequency filters 16 and 21 provide the frequency selection of the signals and separation of the signals having frequency above the "cutoff frequency", which is about 0.1 Hz in correspondence with the lower boundary of the respiratory rate. The separated and amplified signals are then digitized in the analog-to-digital converters 17 and 22 of the first and second channels for processing a return signal.

Figure 20:
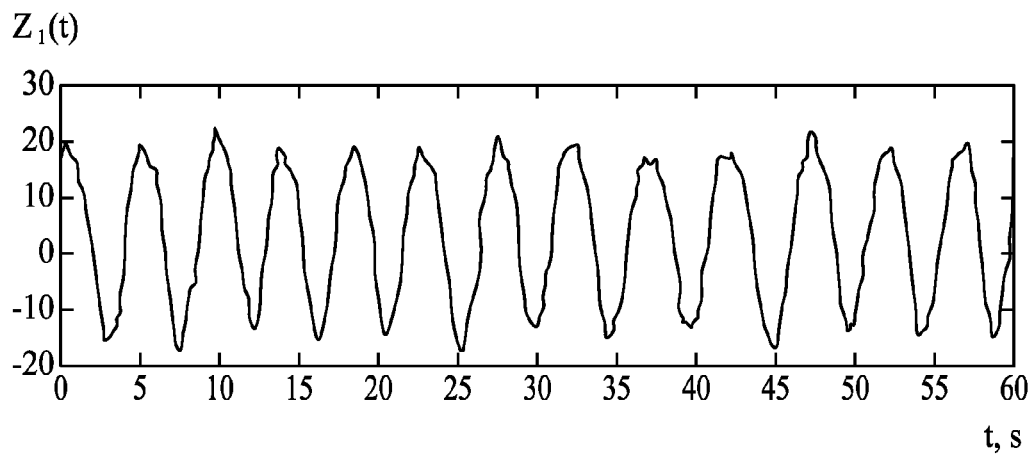
FIG. 20 is a time diagram $Z_1(t)$ of a signal of a first channel for processing a return signal at the input of a first frequency filter.
Figure 22:
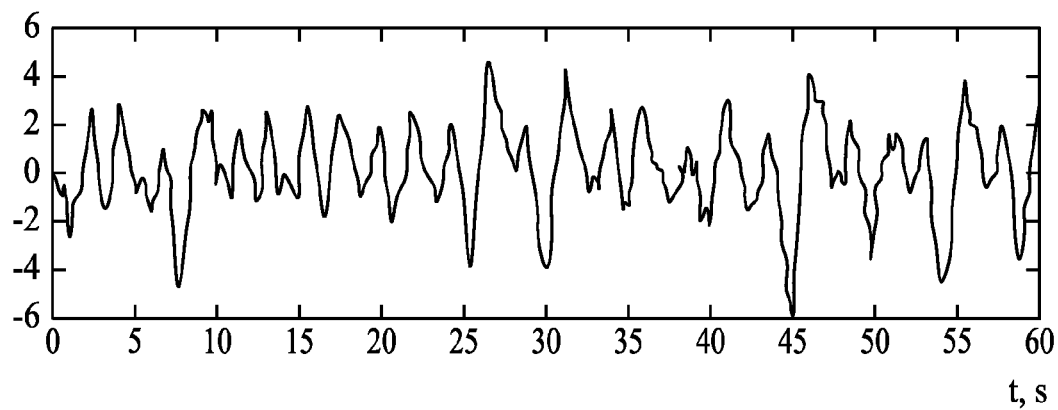
FIG. 22 is a time diagram $Z_2(t)$ of a signal of a second channel for processing a return signal at the input of a second frequency filter.

At the output of the first channel for processing a return signal, a signal $$Z_1(t) = \frac{1}{2} E_m \cos(\varphi(t) + \varphi_1)$$

is formed, which is in phase with the probing reference signal (see FIG. 20). At the output of the second channel for processing a return signal, a signal)

$$Z_2(t) = -\frac{1}{2} E_m \sin(\varphi(t) + \varphi_1)$$

is formed which is phase shifted relative to the probing reference signal by an angle of 90° (see FIG. 22). The given signals are transmitted to the respiratory rate and heart rate calculating path, the structure design of which path is shown in FIGS. 12 and 13.

The signal of the first channel for processing a return signal is sent to the first frequency filter 28, and the signal of the second channel is sent to the second frequency filter 29. The indicated filters having the upper "cutoff frequency" of about 1 Hz provide to remove a high-frequency signal indicative of the heart rate. Thereby the signals indicative of patient's respiration are separated at the output of the frequency filters 28 and 29 from the resultant return signal involving the signals indicative of the patient's chest oscillations and heart rate.

After the frequency selection, the signals from the outputs of the frequency filters 28 and 29 enter the second inputs of the signal adders 30 and 31, the inputs of the third electronic switch 45 and the inputs of the blocks 32 and 33 for calculating a amplitude of the signal. The signals of the first and second channels for processing a return signal are sent to the first inputs of the signal adders 30 and 31, respectively.

The signal adders 30 and 31 operate in a mode of subtracting signals delivered to their inputs. After subtraction of signals indicative of chest oscillations from the composite return signals of the first and second channels for processing a return signal, the signals indicative of patient's heart rate are formed at the outputs of the adders 30 and 31. Discrete signals produced as a result of frequency selection and characterizing various physiological parameters (respiration and heartbeats) are subjected to further correlation processing.

Signal multiplying blocks 40 and 41 and integrators 36 and 37 coupled to the outputs of said blocks are used as a correlation system for processing a signal indicative of a heart rate. The signals from the outputs of adders 30 and 31 are transferred to the first inputs of the signal multiplying blocks 40 and 41. The reference signals from the outputs of the blocks 42 and 43 for generating a reference signal are supplied to the second inputs of the signal multiplying blocks 40 and 41.

In the first version of the present embodiment of the respiratory rate and heart rate calculating path whose block diagram is illustrated in FIG. 12, the blocks 42 and 43 for generating a reference signal are provided with inputs coupled to the outputs of signal adders 30 and 31, respectively. In such a case, fixed lengths of signals under process are used as a reference signal. The duration of such lengths of signals is selected to be equal to at least average oscillation period of a return signal. In an embodiment, the duration of the formed reference signal is 3 seconds.

In certain time intervals, for example with a period of 60 seconds, a length of a signal is recorded by means of blocks 42 and 43 at the output from the respective signal adders 30 and 31 to a memory element. The given length of a signal is used as a reference signal and is transferred to the second input of the respective signal multiplying block (40 or 41) till next recording of a signal length.

In the second version of the present embodiment of the respiratory rate and heart rate calculation path illustrated in FIG. 13, the blocks 42 and 43 are designed for forming a reference signal of constant shape. The signal with a predetermined shape of a curve is stored in memory units of the blocks 42 and 43 and is continuously transferred to the input of the respective signal multiplying block (40 or 41).

In an embodiment, a reference signal is used 1 with a fixed length and a predetermined shape, for example the so-called wavelet described by the following dependence:

$$Z(t) = -(t^2 - 1) \times \exp\left(-\frac{t^2}{2}\right).$$

The duration of such a reference signal is selected to be equal to at least average oscillation period of a return signal. In an embodiment, the duration of the formed signal is 3 seconds.

Figure 21:
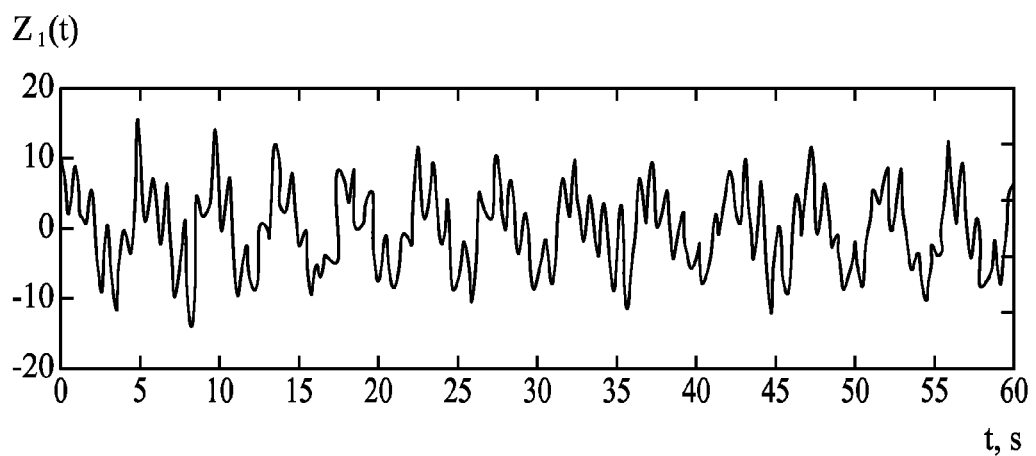
FIG. 21 is a time diagram $Z_1(t)$ of a signal of a first channel for processing a return signal at the output of a first integrator.
Figure 23:
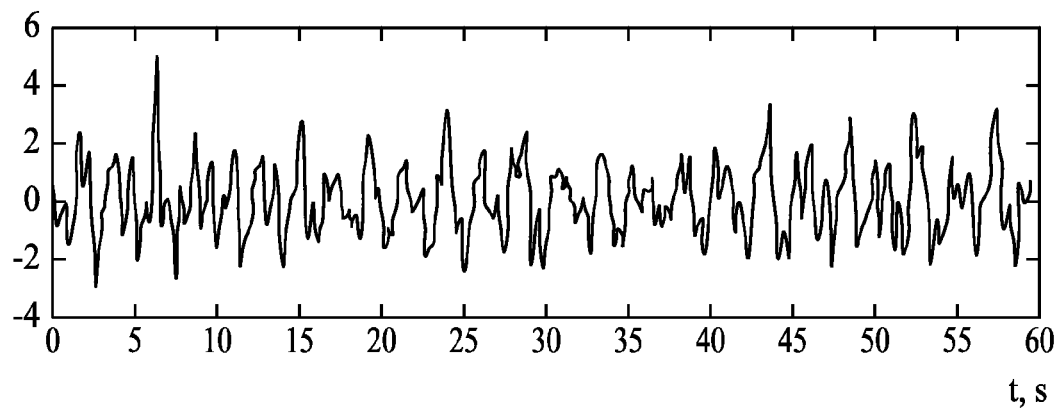
FIG. 23 is a time diagram $Z_2$ (t) of a signal of a second channel for processing a return signal at the output of a second integrator.

Upon multiplying of the incoming signals in the blocks 40 and 41, the reference signal is moved discretely along the signal under process, and the product of multiplying the incoming signals is calculated. The resultant signals from the outputs of the blocks 40 and 41 are transferred to the respective integrators 36 and 37, by means of which integrators the correlation integrals of the signals under process are discretely calculated for each current instant of time. Time diagrams $Z_1(t)$ and $Z_2(t)$ of the signals, respectively, of the first and second channels for processing a return signal at the output of the first and second integrators 36 and 37 are illustrated in FIGS. 21 and 23.

It is obvious from the cited time diagrams $Z_1(t)$ and $Z_2(t)$ of the signals of the first and second channels for processing a return signal that the signal of the first channel at the output of the correlation system (see FIG. 21) is of distinguishable cyclic character and allows the heart rate value to be determined with a high accuracy. The signal of the second channel (see FIG. 23) is of "diffused" non-periodic character, and due to this the heart rate may not be determined with a desired accuracy.

The signals generated in the integrators 36 and 37 are then transferred to the second inputs of the second electronic switch 44 and to the inputs of the signal energy calculating blocks 34 and 35. The signal $Z_1(t)$ enters from the output of the first integrator 36 into the first input of the second electronic switch 44 and into the input of the first signal energy calculating block 34 from the first channel for processing a return signal. The signal $Z_2(t)$ enters from the output of the second integrator 37 into the second input of the second electronic switch 44 and into the input of the second signal energy calculating block 35 from the second channel for processing a return signal.

In order to select a signal which may be further used for precise determining of a heart rate, a procedure for selecting a signal on the basis of its energy value is applied. The energy of the signals delivered from the first and second channels for processing a return signal is determined using the blocks 34 and 35 for calculating energy. The energy of signal in each of the blocks 34 and 35 is determined as a sum of squares of signal amplitude values during a fixed time interval. In an embodiment, the squares of signal amplitude values are calculated during a fixed time interval. The procedure for determining the energy in the blocks 34 and 35 is provided in a real-time mode in which a three-second time interval ("a sliding window") moves along the incoming signal in each measurement.

Figure 24:
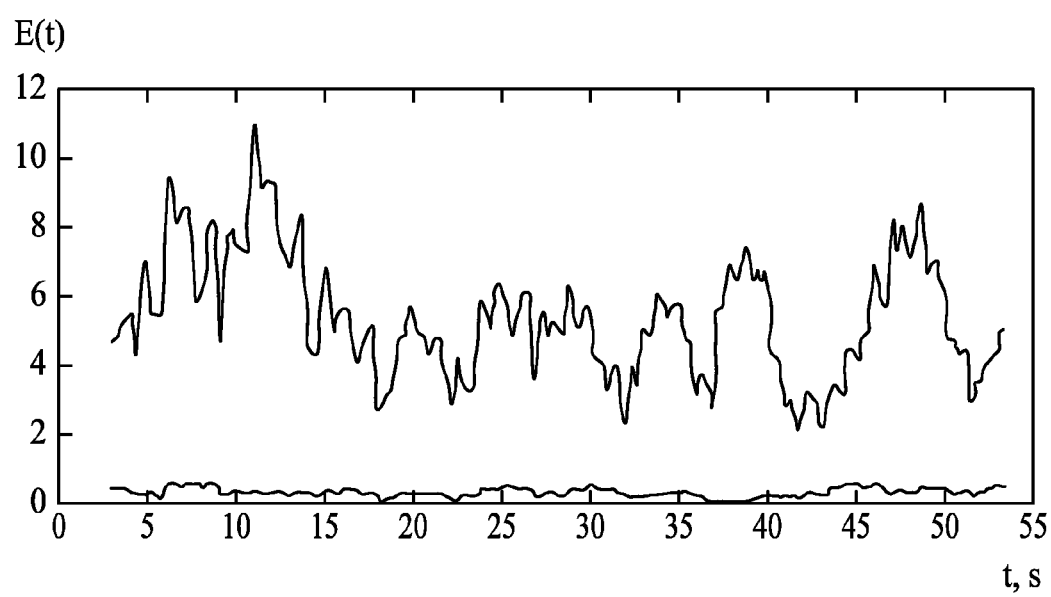
FIG. 24 is a comparative diagram of energy values $E(t)$ of signals at the output of a first (an upper curve) and a second (a lower curve) signal energy calculating blocks.

The calculated signal energy values are then transferred from the outputs of the blocks 34 and 35 respectively to the first and second inputs of the first comparator 38. The comparator 38 allows the incoming signals to be compared and a signal having a greater energy to be defined. A comparative diagram of energy values of the signals E(t) calculated in relative units of measurement is presented in FIG. 24. The upper curve in the comparative diagram E(t) shows variation of the signal energy at the output of the first signal energy calculating block 34. The lower curve in the comparative diagram E(t) characterizes variation of the signal energy at the output of the second signal energy calculating block 35.

It follows from the comparative diagram presented (see FIG. 24) that the signal delivered from the first channel for processing the return signal substantially surpasses the signal delivered from the second channel for processing a return signal in its energy value. Based on the result of comparison of the two incoming signals, the comparator 38 sends the signal to the control input of the second electronic switch 44. The result is that a controlling action is generated for changing the position of the switch contacts, the said changed position should comply with the selected signal of maximum energy. The output of the first integrator 36 is switched to the input of the heart rate calculating block 47 designed for further processing of the selected signal.

Using the heart rate calculating block 47, the local maximum values of the signal under test are searched and time marks (current time values) are defined in conformance with the local maximum values found out. On the basis of the revealed time marks, the patient's heart rate is calculated. The signal indicative of the calculated heart rate value is then transferred to the first input of the data displaying block 48.

In order to select a signal which is to be further used for precise determining of the respiratory rate, a procedure is used for selecting the signal on the basis of amplitude. Utilization of signal amplitude as a criterion in comparing signals at the output of the frequency filters 28 and 29 is due to the low-frequency nature of the curve corresponding to the oscillations of the patient's chest. The respiratory rate is essentially lower in its value, approximately by an order of magnitude, than the heart rate. Therefore, a determining factor for selecting a respiration signal for further processing is the availability of pronounced maximum values of signal amplitude. It is evident from the presented time diagrams $Z_1(t)$ and $Z_2(t)$ of the signals of the first and second channels for processing a return signal that the amplitude of the signal of the first channel substantially surpasses the amplitude of the signal of the second channel. The average range between the opposite signal peaks of the first channel is about 40 units and the respective average range for the second channel is about 3 units (see FIGS. 20 and 22).

The correlation processing of the respiration signals separated using the filters 28 and 29 is carried out by means of two signal amplitude calculating blocks 32 and 33. At the output of the first block 32 is formed a signal indicative of an amplitude of the respiration signal delivered from the first channel for processing a return signal. At the output of the second block 33 is formed a signal indicative of an amplitude of the respiration signal delivered from the second channel for processing a return signal. The signals defining the respiration signal amplitude are transferred from the blocks 32 and 33 to the first and second inputs, respectively, of the second comparator 39.

The values of the two incoming signals from the blocks 32 and 33 for calculating a signal amplitude are compared by comparator 39. On the basis of a comparison result, the comparator 39 sends the signal to the control input of the third electronic switch 45 to generate a control action for changing the position of the switch contacts. The switched connection of contacts should correspond to the selected signal with greater amplitude. In an embodiment, the output of the first frequency filter 28 is connected to the output of the block 46 for calculating a respiratory rate, and the selected signal is delivered from the first channel for processing a return signal to the indicated block for further processing thereof.

Using the block 46 for calculating a respiratory rate, local maximum values of the signal under study are searched and time marks (current time values) are defined in conformance with the local maximum values found. On the basis of the revealed time marks, the patient's respiratory rate is calculated. The signal indicative of the calculated respiratory rate value is then transferred to the second input of the data displaying block 48. The block 48 is used for displaying the results of measurements of the respiratory and heart rates in the form convenient for visual controlling, in particular, in the form of numerical values displayed on a monitor unit.

Figure 25:
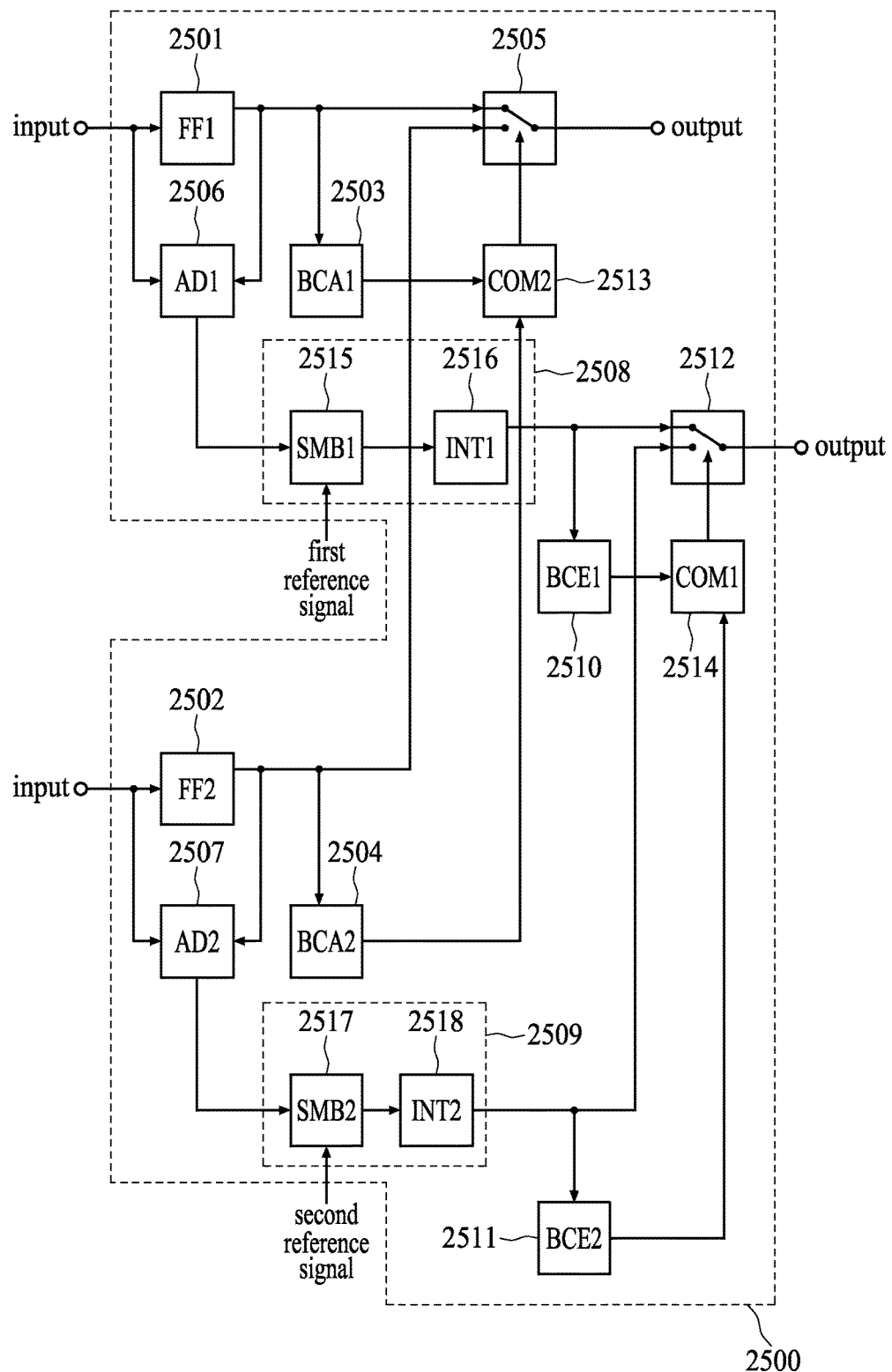
FIG. 25 shows a processing circuit according to one embodiment of the present invention.

FIG. 25 shows a processing circuit according to one embodiment of the present invention. The processing circuit 2500 is applied to a pulsed ultra-wideband sensor for measuring a respiratory rate and a heart rate, such as the pulsed ultra-wideband sensors according to embodiments of the present invention, and comprises a first frequency filter 2501, a second frequency filter 2502, a first signal amplitude calculator 2503, a second signal amplitude calculator 2504, a first electronic switch 2505, a first adder 2506, a second adder 2507, a first signal integrator 2508, a second signal integrator 2509, a first signal energy calculator 2510, a second signal energy calculator 2511 a second electronic switch 2512, a first comparator 2513 and a first comparator 2514.

The first frequency filter 2501 is configured to receive an in-phase signal, such as the output signal of the ADC 17. The second frequency filter 2502 is configured to receive a quadrature signal, such as the output signal of the ADC 22. The first signal amplitude calculator 2503 is configured to calculate the amplitude of the output signal of the first frequency filter 2501. The second signal amplitude calculator 2504 is configured to calculate the amplitude of the output signal of the second frequency filter 2502. The first electronic switch 2505 is configured to output one of the output signals of the first and the second frequency filters 2501 and 2502 according to the calculated results of the first and the second signal amplitude calculators 2503 and 2504. The first adder 2506 is configured to subtract the output signal of the first frequency filter 2501 from the input signal of the first frequency filter 2501. The second adder 2507 is configured to subtract the output signal of the second frequency filter 2502 from the input signal of the second frequency filter 2502. The first signal integrator 2508 is configured to calculate correlation integrals of the output signals of the first adder 2506 and a first reference signal. The second signal integrator 2509 is configured to calculate correlation integrals of the output signals of the second adder 2507 and a second reference signal. The first signal energy calculator 2510 is configured to calculate signal energy of the output signal of the first signal integrator 2508. The second signal energy calculator 2511 is configured to calculate signal energy of the output signal of the second signal integrator 2509. The second electronic switch 2512 is configured to output one of the output signals of the first and the second signal integrators 2508 and 2509 according to the calculated results of the first and the second signal energy calculators 2510 and 2511.

In some embodiments, the first signal integrator 2508 comprises a first signal multiplier 2515 and a first integrator 2516. The first signal multiplier 2515 is configured to multiply the output signal of the first adder 2506 by the first reference signal. The first integrator 2516 is configured to calculate the integral of the output signal of the first signal multiplier 2515. In other embodiments, the second signal integrator 2509 comprises a second signal multiplier 2517 and a second integrator 2518. The second signal multiplier 2517 is configured to multiply the output signal of the second adder 2507 by the second reference signal. The second integrator 2518 is configured to calculate the integral of the output signal of the second signal multiplier 2517. In some embodiments, the processing circuit 2500 further comprises a first comparator 2513 and a second comparator 2514. The first comparator 2513 is configured to compare the calculated results of the first and the second signal amplitude calculators 2503 and 2504 and control the first electronic switch 2505. The second comparator 2514 is configured to compare the calculated results of the first and the second signal energy calculators 2510 and 2511 and control the second electronic switch 2512. In some embodiments, the first reference signal and the second reference signal exhibit a constant shape. In other embodiments, the first reference signal is generated according to the output signal of the first adder 2506, while the second reference signal is generated according to the output signal of the second adder 2507. In some embodiments, the processing circuit 2500 further comprises a first reference signal generating block for the generation of the first reference signal, and a second reference signal generating block for the generation of the second reference signal.

The sensor implemented according to the invention allows the frequency selection of the return signal to be executed in the two processing channels, independent signals describing the respiratory rate to be selected separately from other signals describing the heart rate, separate correlation processing of the separated signals to be provided, and, thereafter, the signal with greater high amplitude or energy for respiratory rate or heart rate, respectively, to be selected for each of the physiological parameters under study for further calculation of the respiratory and heart rate values with a desired accuracy. However, the physiological parameters measured according to the sensor and the method thereof are not limited to respiratory rate or heart rate, but can also applied to other physiological parameters such as intestinal motility.

The given procedure for processing the return signal, realized using a certain structured design of the path for calculating the respiratory and heart rate values, allows a phase sensitivity of the sensor and measurement accuracy of the physiological parameters under study to be significantly increased. In addition, there appears the possibility of measuring the parameters upon movement of the subjects under study thanks to the elimination of influence upon the measurement results of the "blind" zones at the working distance of the sensor.

The pulsed ultra-wideband sensor may be employed in medical equipment as a high-sensitive means for cardiovascular system and respiratory organs diagnosis under stationary and field conditions.

A list of digital and abbreviated letter symbols of structural elements of a pulsed ultra-wideband sensor, depicted in FIGS. 10, 11, 12, and 13 on the accompanying drawings:
  1—control unit (CU);
  2—self-contained microwave generator (SMG);
  3—transmitting antenna;
  4—receiving antenna;
  5—first electronic switch;
  6—buffer amplifier (BA);
  7—band pass filter for a probing signal (BFPS);
  8—bans pass filter for a transmitter (BFT);
  9—transmitter amplifier (TA);

10—band pass filter for a return signal (BFRS);
11—low-noise amplifier (LNA);
12—phase-shifting circuit (PSC);
13—signal mixer of a first channel for processing a return signal (SM1);
14—band pass filter of a first channel for processing a return signal (BF1);
15—low-frequency amplifier of a first channel for processing a return signal (LFA1);
16—low-frequency filter of a first channel for processing a return signal (LFF1);
17—analog-to-digital converter of a first channel for processing a return signal (ADC1);
18—signal mixer of a second channel for processing a return signal (SM2);
19—band pass filter of a second channel for processing a return signal (BF2);
20—low-frequency amplifier of a second channel for processing a return signal (LFA2);
21—low-frequency filter of a second channel for processing a return signal (LFF2);
22—analog-to-digital converter of a second channel for processing a return signal (ADC2);
23—driving generator of a control unit (DG);
24—first short-pulse former of a control unit (SPF1);
25—digital delay line of a control unit (DDL);
26—second short-pulse former of a control unit (SPF2);
27—"OR" circuit of a control unit;
28—first frequency filter (FF1);
29—second frequency filter (FF2);
30—first adder (AD1);
31—second adder (AD2);
32—first block for calculating a signal amplitude (BCA1);
33—second block for calculating a signal amplitude (BCA2);
34—first block for calculating a signal energy (BCE1);
35—second block for calculating a signal energy (BCE2);
36—first integrator (INT1);
37—second integrator (INT2);
38—first comparator (COM1);
39—second comparator (COM2);
40—first signal multiplying block (SMB1);
41—second signal multiplying block (SMB2);
42—first block for generating a reference signal (GRS1);
43—second block for generating a reference signal (GRS2);
44—second electronic switch;
45—third electronic switch;
46—respiratory rate calculating block (BCR);
47—heart rate calculating block (BCH);
48—data display block (DDB);
2500—processing circuit;
2501—first frequency filter (FF1);
2502—second frequency filter (FF2);
2503—first signal amplitude calculator (BCA1);
2504—second signal amplitude calculator (BCA2);
2505—first electronic switch;
2506—first adder (AD1);
2507—second adder (AD2);
2508—first signal integrator;
2509—second signal integrator;
2510—first signal energy calculator (BCE1);
2511—second signal energy calculator (BCE2);
2512—second electronic switch;
2513—first comparator (COM1);
2514—second comparator (COM2);
2515—first signal multiplier (SMB1);
2516—first integrator (INT1);
2517—second signal multiplier (SMB2);
2518—second integrator (INT2).

What is claimed is:

1. A pulsed ultra-wideband sensor, comprising:
an antenna configured to receive a return signal;
a signal generator configured to generate a first synchronizing signal;
a phase shift circuit configured to generate a second synchronizing signal having a phase shift with respect to the first synchronizing signal;
a first receiver for generating a first signal in time domain in response to the return signal and the first synchronizing signal, the first signal including information on a first physiological parameter and a second physiological parameter;
a second receiver for generating a second signal in time domain in response to the return signal and the second synchronizing signal, the second signal including information on the first physiological parameter and the second physiological parameter, the first signal and the second signal being in quadrature, and thereby at least one of the first signal and the second signal is not degraded due to the blind-zone effect;
a first detector for detecting the first physiological parameter in response to the first signal from the first receiver and the second signal from the second receiver; and
a second detector for detecting the second physiological parameter in response to the first signal from the first receiver and the second signal from the second receiver.

2. The pulsed ultra-wideband sensor of claim 1, further comprising
a transmitter for transmitting a probing signal, wherein the signal generator is further configured to generate a third synchronizing signal for the transmitter.

3. The pulsed ultra-wideband sensor of claim 2, wherein the signal generator comprises:
a driving generator configured to generate a pulse;
a delay line configured to provide a delayed pulse in response to the pulse from the driving generator;
a first pulse former configured to generate the first synchronizing signal in response to the delayed pulse from the delay line;
a second pulse former configured to generate a pulse signal in response to the pulse from the driving generator; and
a circuit configured to generate the second synchronizing signal by summing the first synchronizing signal and the pulse signal.

4. The pulsed ultra-wideband sensor of claim 1, wherein first detector comprises:
a first frequency filter configured to provide, in response to the first signal, a first filtered signal having a band below a cutoff frequency; and
a second frequency filter configured to provide, in response the second signal, a second filtered signal having the band.

5. The pulsed ultra-wideband sensor of claim 4, wherein the first detector further comprises:
a first signal amplitude calculator configured to determine a first amplitude of the first filtered signal;
a second signal amplitude calculator configured to determine a second amplitude of the second filtered signal;
a first comparator configured to select one of the first filtered signal and the second filtered signal based on the first amplitude and the second amplitude; and a first electronic switch configured to, in response to a result of selection from the first comparator, switch between the first filtered signal and the second filtered signal for determining the first physiological parameter.

6. The pulsed ultra-wideband sensor of claim 1, wherein the second detector comprises:
   a first filter for providing, in response to the first signal, a first filtered signal having a first band above a cutoff frequency; and
   a second filter for providing, in response the second signal, a second filtered signal having the first band.

7. The pulsed ultra-wideband sensor of claim 6, further comprising:
   a first frequency filter configured to provide a third filtered signal in response to the first signal, the third filtered signal having a second band below the cutoff frequency;
   a first adder configured to provide the first filtered signal by subtracting the third filtered signal from the first signal;
   a second frequency filter configured to provide a fourth filtered signal in response to the second signal, the fourth filtered signal having the second band; and
   a second adder configured to provide the second filtered signal by subtracting the fourth signal from the second signal.

8. The pulsed ultra-wideband sensor of claim 6, wherein the second signal detector further comprises:
   a first signal integrator configured to provide a first integrated signal by integrating the first filtered signal with a first reference signal;
   a second signal integrator configured to provide a second integrated signal by integrating the second filtered signal with a second reference signal;
   a first signal energy calculator configured to determine a first energy value of the first integrated signal;
   a second signal energy calculator configured to determine a second energy value of the second integrated signal;
   a second comparator configured to select one of the first integrated signal and the second integrated signal based on the first energy value and the second energy value; and
   a second electronic switch configured to, in response to a result of selection from the second comparator, switch between the first integrated signal and the second integrated signal for determining the second physiological parameter.

9. A method for operating a pulsed ultra-wideband sensor, comprising:
   receiving a return signal by an antenna;
   generating a first synchronizing signal;
   generating a second synchronizing signal having a phase shift with respect to the first synchronizing signal;
   generating a first signal in time domain in response to the return signal and the first synchronizing signal, the first signal including information on a first physiological parameter and a second physiological parameter;
   generating a second signal in time domain in response to the return signal and the second synchronizing signal, the second signal including information on the first physiological parameter and the second physiological parameter, the first signal and the second signal being in quadrature, and thereby at least one of the first signal and the second signal is not degraded due to the blind-zone effect;
   detecting the first physiological parameter in response to the first signal and the second signal; and
   detecting the second physiological parameter in response to the first signal and the second signal.

10. The method of claim 9, wherein the pulsed ultra-wideband sensor comprises a transmitter, the method further comprising:
    generating a third synchronizing signal for the transmitter.

11. The method of claim 10, further comprising:
    generating a pulse;
    providing a delayed pulse in response to pulse;
    generating the first synchronizing signal in response to the delayed pulse;
    generating a pulse signal in response to the pulse; and
    generating the second synchronizing signal by summing the first synchronizing signal and the pulse signal.

12. The method of claim 9, wherein the step of detecting the first physiological parameter comprises:
    providing, in response to the first signal, a first filtered signal having a band below a cutoff frequency; and
    providing, in response the second signal, a second filtered signal having the band.

13. The method of claim 12, wherein the step of detecting the first physiological parameter further comprises:
    determining a first amplitude of the first filtered signal;
    determining a second amplitude of the second filtered signal;
    selecting one of the first filtered signal and the second filtered signal based on the first amplitude and the second amplitude; and
    switching, in response to a result of the selecting, between the first filtered signal and the second filtered signal for determining the first physiological parameter.

14. The method of claim 9, wherein the step of detecting the second physiological parameter comprises:
    providing, in response to the first signal, a first filtered signal having a first band above a cutoff frequency; and
    providing, in response the second signal, a second filtered signal having the first band.

15. The method of claim 14, wherein
    the step of providing the first filtered signal comprises providing the first filtered signal by subtracting from the first signal a third filtered signal having a second band below the cutoff frequency; and
    the step of providing the second filtered signal comprises providing the second filtered signal by subtracting from the second signal a fourth filtered signal having the second band.

16. The method of claim 14, wherein step of detecting the second physiological parameter further comprises:
    providing a first integrated signal by integrating the first filtered signal with a first reference signal;
    providing a second integrated signal by integrating the second filtered signal with a second reference signal;
    determining a first energy value of the first integrated signal;
    determining a second energy value of the second integrated signal;
    selecting one of the first integrated signal and the second integrated signal based on the first energy value and the second energy value; and
    switching, in response to a result of the selecting, between the first integrated signal and the second integrated signal for determining the second physiological parameter;
    the step of providing the second integrated signal further comprises integrating the second filtered signal with the second filtered signal.

* * * * *